US007959922B2

(12) United States Patent
Bakker et al.

(10) Patent No.: US 7,959,922 B2
(45) Date of Patent: Jun. 14, 2011

(54) LIQUID ANTI-RABIES ANTIBODY FORMULATIONS

(75) Inventors: Alexander B. H. Bakker, Leiden (NL); Willem E. Marissen, Leiden (NL)

(73) Assignee: Crucell Holland B.V., Leiden (NL)

( * ) Notice: Subject to any disclaimer, the term of this patent is extended or adjusted under 35 U.S.C. 154(b) by 0 days.

(21) Appl. No.: 12/312,967

(22) PCT Filed: Dec. 4, 2007

(86) PCT No.: PCT/EP2007/063244
§ 371 (c)(1),
(2), (4) Date: Jun. 2, 2009

(87) PCT Pub. No.: WO2008/068246
PCT Pub. Date: Jun. 12, 2008

(65) Prior Publication Data
US 2010/0034829 A1 Feb. 11, 2010

Related U.S. Application Data

(60) Provisional application No. 60/872,892, filed on Dec. 5, 2006.

(30) Foreign Application Priority Data

Dec. 5, 2006 (EP) .................................... 06125400

(51) Int. Cl.
*A61K 39/42* (2006.01)
(52) U.S. Cl. ................................. 424/147.1; 530/388.3
(58) Field of Classification Search .................. None
See application file for complete search history.

(56) References Cited

U.S. PATENT DOCUMENTS

| 7,579,446 B2 * | 8/2009 | Bakker et al. ............. 530/387.3 |
| 7,740,852 B2 | 6/2010 | Bakker et al. |
| 2004/0013672 A1 | 1/2004 | Hooper et al. |
| 2006/0263802 A1 | 11/2006 | Bakker et al. |
| 2008/0070799 A1 | 3/2008 | Bakker et al. |
| 2010/0272724 A1 | 10/2010 | Bakker et al. |
| 2010/0310572 A1 | 12/2010 | Bakker et al. |

FOREIGN PATENT DOCUMENTS

| AU | 7198291 A1 | 9/1991 |
| EP | 0 402 029 | 12/1990 |
| EP | 0 445 625 | 9/1991 |
| WO | WO 98/15833 | 4/1998 |
| WO | WO 03/016501 | 2/2003 |
| WO | WO 2004/009618 | 1/2004 |
| WO | WO 2005/023849 | 3/2005 |
| WO | WO 2005/118644 * | 12/2005 |
| WO | WO 2006/112838 * | 10/2006 |
| WO | WO 2008/068246 A1 | 6/2008 |

OTHER PUBLICATIONS

Prosniak et al (Journal of Infectious Diseases 188:53-56, 2003).*
Champion et al (Journal of Immunological Methods 235:81-90, 2000).*
Wang et al (Journal of Pharmaceutical Sciences 96:1-26, 2007).*
PCT International Search Report, PCT/EP2007/063244, dated Apr. 2, 2008.
PCT Written Opinion, PCT/EP2007/063244 dated Apr. 2, 2008.
Notice of Allowance for U.S. Appl. No. 10/517,941 dated Apr. 8, 2009.
Office Action for U.S. Appl. No. 11/317,786 dated Mar. 17, 2009.
Notice of Allowance for U.S. Appl. No. 11/590,126 dated Apr. 10, 2009.
Office Action for U.S. Appl. No. 11/978,742 dated Mar. 25, 2009.
Kramer et al., Abstract, Immunity to infection: The human antibody repertoire specific for rabies virus glycoprotein as selected from immune libraries, Eur. J. Immunol., 35: 2131-2145 (2005).
Schumacher et al. "Use of mouse anti-rabies monoclonal antibodies in post-exposure treatment of rabies." J. Clin. Invest. 84:971-975 (1989).
Paul, Fundamental Immunology, (textbook), 1993, pp. 292-95, Lippincott-Raven Publishers, Philadelphia, PA.
Database Genbank NCBI; Jun. 26, 2003, Prosniak, M. et al., "*Homo sapieans* anti-rabies S057 immunoglobul in heavy chain mRNA" XP 002356864, retrieved from http://www.ncbi.nlr.nih.gov, Database accession No. AY172957.
Database Genbank NCBI; Jun. 26, 2003, Prosniak, M. et al., "*Homo sapieans* anti-rabies S057 immunoglobul in lambda light chain mRNA" XP 002356865, retrieved from http://www.ncbi.nlr.nih.gov, Database accession No. AY172960.
PCT International Search Report, PCT/EP2005/052410, dated Jan. 1, 2006.
PCT International Preliminary Report on Patentability, PCT/EP2005/052410, dated Aug. 28, 2006.
Prosniak et al., "Development of a Cocktail of Recombinant-Expressed Human Rabies Virus-Neutralizing Monoclonal Antibodies for Postexposure Prophylaxis of Rabies," Journal of Infectious Diseases, Jul. 1, 2003, pp. 53-56, vol. 188.
Champion et al., "The development of monoclonal human rabies virus-neutralizing antibodies as a substitute for pooled human immune globulin in the prophylactic treatment of rabies virus exposure," Journal of Immunological Methods, 2000, pp. 81-90, vol. 235.
Dietzschold et al., "Biological Characterization of Human Monoclonal Antibodies to Rabies Virus," Journal of Virology, Jun. 1990, pp. 3087-3090, vol. 64, No. 6.
Hanlon et al., "Experimental utility of rabies virus-neutralizing human monoclonal antibodies in post-exposure prophylaxis," Vaccine, 2001, pp. 3834-3842, vol. 19.
Jones et al., "High-level Expression of Recombinant IgG in the Human Cell Line Per.C6," Biotechnol. Prog., 2003, pp. 163-168, vol. 19.
De Kruif et al., "Selection and Application of Human Single Chain Fv Antibody Fragments from a Semi-synthetic Phage Antibody Display Library with Designed CDR3 Regions." J. Mol. Biol., 1995, pp. 97-105, vol. 248.
U.S. Appl. No. 10/517,941, filed Dec. 13, 2004, Inventor: Bakker et al, Title: Antibody to the Human OX40 Receptor.
U.S. Appl. No. 11/317,786, filed Dec. 22, 2005, Inventor: van den Oudenrijn et al., Title: Binding Molecules for the Treatment of Myeloid Cell Malignancies.
U.S. Appl. No. 11/590,126, filed Oct. 31, 2006, Inventor: Bakker et al., Title: Binding Molecules Capable of Neutralizing Rabies Virus and Uses Thereof.

(Continued)

Primary Examiner — Mary E Mosher
(74) Attorney, Agent, or Firm — TraskBritt, P.C.

(57) ABSTRACT

The present invention provides pharmaceutical antibody formulations, in particular liquid pharmaceutical formulations comprising anti-rabies virus antibodies. The formulations can be used in the post exposure prophylaxis of rabies.

18 Claims, 3 Drawing Sheets

OTHER PUBLICATIONS

U.S. Appl. No. 11/978,742, filed Oct. 29, 2007, Inventor: Bakker et al., Title: Binding Molecules Capable of Neutralizing Rabies Virus and Uses Thereof.

U.S. Appl. No. 11/980,237, filed Oct. 29, 2007, Inventor: Bakker et al., Title: Binding Molecules Capable of Neutralizing Rabies Virus and Uses Thereof.

U.S. Appl. No. 12/383,330, filed Mar. 23, 2009, Inventor: Bakker et al., Title: Agonistic Binding Molecules to the Human OX40 Receptor.

Daugherty et al., Formulation and delivery issues for monoclonal antibody therapeutics, Advanced Drug Delivery Reviews, 2006, pp. 686-706, vol. 58, Science Direct.

PCT International Preliminary Report on Patenability, PCT/EP2004/052043, dated Dec. 21, 2005.

PCT International Search Report, PCT/EP2004/052043, dated Apr. 21, 2005.

Database Geneseq 'Online! Dec. 18, 2003, "Wild-type rabies virus G protein." XP002323001, retrieved from EBI accession No. GSN:ACD37470, Database accession No. ADC37470.

Database USPTO Proteins "Online! May 14, 2004. "Sequence 59 from patent US 6,706,523." XP002323002, retrieved from EBI accession No. USPOP:AAT21621, Database accession No. AAT21621.

Database Geneseq 'Online! Dec. 18, 2003, "Mutant rabies virus G protein," XP002323003, retrieved from EBI accession No. GSN:ADC37471, Database accession No. ADC37471.

Database USPTO Proteins "Online! May 14, 2004, "Sequence 60 from patent US 6,706,523." XP002323004, retrieved from EBI accession No. USPOP:AAT21622, Database accession No. AAT21622.

Fodor et al., "Nucleotide and deduced amino acid sequences of the glycoprotein gene of rabies virus vaccine strain Vnukovo-32," Archives of Virology, 1994, pp. 451-459, vol. 135, No. 3-4.

Database NCBI ' Online! Jun. 1, 2001, Jayakumar: XP0002323005, retrieved from EBI accession No. Q99AU1. Database accession No. Q99AU1.

Database JPO Proteins 'Online! Apr. 27, 1998, "A recombinant Glycoprotein," XP002323006, retrieved from EBI accession No. JPOP:E61000, Database accession No. E61000.

Database Geneseq 'Online! Mar. 21, 1997, "Recombinant abies virus G protein," XP002323007, retrieved from EBI accession No. GSN:AAW09380, Database accession No. AAW09380.

Dietzschold et al., "Chemical and Immunological Analysis of the rabies Soluble Glycoprotein," Virology, 1983, pp. 330-337, vol. 124, No. 2.

Benmansour et al., Antigenicity of Rabies Virus Glycoprotein, Journal of Virology, 1991, pp. 4198-4203, vol. 65, No. 8.

De Haard et al., A Large Non-immunized Human Fab Fragment Phage Library That Permits Rapid Isolation and Kinetic Analysis of High Affinity Antibodies. 1999, Journal of Biological Chemistry, pp. 18218-18230, vol. 274, No. 26.

De Kruif et al., Rapid selection of cell subpopulation-specific human monoclonal antibodies from a synthetic phage antibody library, 1995, Proceedings of the National Academy of Sciences of the United States of America. vol. 92, pp. 3938-3942.

Dietzschold et al., "New Approaches to the Development of Live Attenuated Rabies Vaccines," Hybridoma and Hybridomics, Apr. 2002, pp. 129-134, vol. 21, No. 2.

Dietzschold et al., "Structural and Immunological Characterization of a Linear Virus-Neutralizing Epitope of the Rabies Virus glycoprotein and its Possible Use in a Synthetic Vaccine," Journal of Virology, Aug. 1990, pp. 3804-3809, vol. 64, No. 8.

Drings et al., "Is there an advantage to including the nucleoprotein in a rabies glycoprotein subunit vaccine?" Vaccine, 1999, pp. 1549-1557, vol. 17, No. 11/12.

Fu et al., "Oral vaccination of raccoons (*Procyon lotor*) with baculovirus-expressed rabies virus glycoprotein," Vaccine, 1993, pp. 925-928, vol. 11, No. 9.

Luo et al., "A virus-neutralizing epitope on the glycoprotein of rabies virus that contains Trp251 is a linear epitope," Virus Research, 1997, pp. 35-41, vol. 51, No. 1.

McGarvey et al., "Expression of the rabies Virus Glycoprotein in Transgenic Tomatoes," Bio/Technology, Dec. 1995, pp. 1484-1487, Vo. 13.

Morimoto et al., "Shedding of Gs Protein (A Soluble Form of the Viral Glycoprotein) by the Rabies Virus-Infected BHK-21 Cells," Virology, 1993, pp. 541-549, vol. 195, No. 2.

Xuan et al., "Biological and immunogenic properties of rabies virus glycoprotein expressed by canine herpesvirus vector," Vaccine, 1998, pp. 969-976, vol. 16, No. 9/10.

Heitner et al., Selection of cell binding and internalizing epidermal growth factor receptor antibodies from a phage display library, Journal of Immunological Methods, 2001, pp. 17-30, vol. 248.

Ikematsu et al., Sequences of the Vh genes of human IgM, IgG and IgA to rabies virus reveal preferential utilization of VhIII segments and somatic hypermutation, 1993, The Journal of Immunology, pp. 1325-1337, vol. 150.

Lang et al., Abstract, Evaluation of the Safety and Immunogenicity of a New, Heat-treated Human Rabies Immune Globulin Using a Sham, Post-exposure Prophylaxis of Rabies, Biologicals, 1998, vol. 26, No. 7-15.

Leucht et al., The B cell superantigen-like interaction of intravenous immunoglobulin (IVIG) with Fab fragments of Vh 3-23 and 3-30/3-30.5 germline gene origin cloned from a patient with Kawasaki disease is enhanced after IVIG therapy, 2001. Clinical Immunology, pp. 18-29, vol. 99.

Marissen et al., Novel Rabies Virus-Neutralizing Epitope Recognized by Human Monoclonal Antibody: Fine Mapping and Escape Mutant Analysis, Journal of Virology, Apr. 2005, pp. 4672-4678, vol. 79, No. 8.

Nicacio et al., Neutralizing human fab fragments against measles virus recovered by phage display, Journal of Virology, 2002, pp. 251-258, vol. 76.

Ray et al., Selection of single chain variable fragments (scFv) against the glycoprotein antigen of the rabies virus from a human synthetic scFv phage display library and their fusion with the Fc region of human IgG1, Clinical and Experimental Immunology, 2001, pp. 94-101, vol. 125.

* cited by examiner

SEQUENCE LISTING

<160> NUMBER OF SEQ ID NOS: 4

<210> SEQ ID NO 1
<211> LENGTH: 457
<212> TYPE: PRT
<213> ORGANISM: Homo sapiens
<220> FEATURE:
<221> NAME/KEY: CR57 heavy chain
<222> LOCATION: (1)..(457)

<400> SEQUENCE: 1

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Arg Tyr
            20                  25                  30

Thr Val Asn Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Arg Phe
    50                  55                  60

Gln Gly Arg Leu Thr Ile Thr Ala Asp Glu Ser Thr Ser Thr Ala Tyr
65                  70                  75                  80

Met Glu Leu Ser Ser Leu Arg Ser Asp Thr Ala Val Tyr Phe Cys
                85                  90                  95

Ala Arg Glu Asn Leu Asp Asn Ser Gly Thr Tyr Tyr Phe Ser Gly
            100                 105                 110

Trp Phe Asp Pro Trp Gly Gln Gly Thr Leu Val Thr Val Ser Ser Ala
            115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Leu Gly Thr Gln Thr Tyr
    195                 200                 205

Ile Cys Asn Val Asn His Lys Pro Ser Asn Thr Lys Val Asp Lys Arg
210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350
```

```
Pro Arg Glu Pro Gln Val Tyr Thr Leu Pro Pro Ser Arg Glu Glu Met
            355                 360                 365

Thr Lys Asn Gln Val Ser Leu Thr Cys Leu Val Lys Gly Phe Tyr Pro
370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
            405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
            435                 440                 445

Lys Ser Leu Ser Leu Ser Pro Gly Lys
            450                 455

<210> SEQ ID NO 2
<211> LENGTH: 218
<212> TYPE: PRT
<213> ORGANISM: Homo sapiens
<220> FEATURE:
<221> NAME/KEY: CR57 light chain
<222> LOCATION: (1)..(218)

<400> SEQUENCE: 2

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Ile Gly Gly Tyr
                20                  25                  30

Asn Phe Val Ser Trp Tyr Gln Gln His Pro Gly Lys Ala Pro Lys Leu
            35                  40                  45

Met Ile Tyr Asp Ala Thr Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Asp
                85                  90                  95

Tyr Thr Pro Gly Val Val Phe Gly Gly Gly Thr Lys Leu Thr Val Leu
            100                 105                 110

Gly Gln Pro Lys Ala Ala Pro Ser Val Thr Leu Phe Pro Pro Ser Ser
            115                 120                 125

Glu Glu Leu Gln Ala Asn Lys Ala Thr Leu Val Cys Leu Ile Ser Asp
            130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
            195                 200                 205

Glu Lys Thr Val Ala Pro Thr Glu Cys Ser
            210                 215

<210> SEQ ID NO 3
<211> LENGTH: 449
<212> TYPE: PRT
<213> ORGANISM: Homo sapiens
```

```
<220> FEATURE:
<221> NAME/KEY: CR4098 heavy chain
<222> LOCATION: (1)..(449)

<400> SEQUENCE: 3
```

| | | | | | | | | | | | | | | |
|---|---|---|---|---|---|---|---|---|---|---|---|---|---|---|
| Gln | Val | Gln | Leu | Val | Glu | Ser | Gly | Gly | Ala | Val | Gln | Pro | Gly | Arg |
| 1 | | | | 5 | | | | | 10 | | | | | 15 |
| Ser | Leu | Arg | Leu | Ser | Cys | Ala | Ala | Ser | Gly | Phe | Thr | Phe | Ser | Ser |
| | | | 20 | | | | | 25 | | | | | 30 | |
| Tyr | Gly | Met | His | Trp | Val | Arg | Gln | Ala | Pro | Gly | Lys | Gly | Leu | Glu |
| | | | 35 | | | | | 40 | | | | | 45 | |
| Trp | Val | Ala | Val | Ile | Leu | Tyr | Asp | Gly | Ser | Asp | Lys | Phe | Tyr | Ala |
| | | 50 | | | | | 55 | | | | | 60 | | |
| Asp | Ser | Val | Lys | Gly | Arg | Phe | Thr | Ile | Ser | Arg | Asp | Asn | Ser | Lys |
| | | | 65 | | | | | 70 | | | | | 75 | |
| Asn | Thr | Leu | Tyr | Leu | Gln | Met | Asn | Ser | Leu | Arg | Ala | Glu | Asp | Thr |
| | | | 80 | | | | | 85 | | | | | 90 | |
| Ala | Val | Tyr | Tyr | Cys | Ala | Lys | Val | Ala | Val | Ala | Gly | Thr | His | Phe |
| | | | 95 | | | | | 100 | | | | | 105 | |
| Asp | Tyr | Trp | Gly | Gln | Gly | Thr | Leu | Val | Thr | Val | Ser | Ser | Ala | Ser |
| | | | 110 | | | | | 115 | | | | | 120 | |
| Thr | Lys | Gly | Pro | Ser | Val | Phe | Pro | Leu | Ala | Pro | Ser | Ser | Lys | Ser |
| | | | 125 | | | | | 130 | | | | | 135 | |
| Thr | Ser | Gly | Gly | Thr | Ala | Ala | Leu | Gly | Cys | Leu | Val | Lys | Asp | Tyr |
| | | | 140 | | | | | 145 | | | | | 150 | |
| Phe | Pro | Glu | Pro | Val | Thr | Val | Ser | Trp | Asn | Ser | Gly | Ala | Leu | Thr |
| | | | 155 | | | | | 160 | | | | | 165 | |
| Ser | Gly | Val | His | Thr | Phe | Pro | Ala | Val | Leu | Gln | Ser | Ser | Gly | Leu |
| | | | 170 | | | | | 175 | | | | | 180 | |
| Tyr | Ser | Leu | Ser | Ser | Val | Val | Thr | Val | Pro | Ser | Ser | Ser | Leu | Gly |
| | | | 185 | | | | | 190 | | | | | 195 | |
| Thr | Gln | Thr | Tyr | Ile | Cys | Asn | Val | Asn | His | Lys | Pro | Ser | Asn | Thr |
| | | | 200 | | | | | 205 | | | | | 210 | |
| Lys | Val | Asp | Lys | Arg | Val | Glu | Pro | Lys | Ser | Cys | Asp | Lys | Thr | His |
| | | | 215 | | | | | 220 | | | | | 225 | |
| Thr | Cys | Pro | Pro | Cys | Pro | Ala | Pro | Glu | Leu | Leu | Gly | Gly | Pro | Ser |
| | | | 230 | | | | | 235 | | | | | 240 | |
| Val | Phe | Leu | Phe | Pro | Pro | Lys | Pro | Lys | Asp | Thr | Leu | Met | Ile | Ser |
| | | | 245 | | | | | 250 | | | | | 255 | |
| Arg | Thr | Pro | Glu | Val | Thr | Cys | Val | Val | Val | Asp | Val | Ser | His | Glu |
| | | | 260 | | | | | 265 | | | | | 270 | |
| Asp | Pro | Glu | Val | Lys | Phe | Asn | Trp | Tyr | Val | Asp | Gly | Val | Glu | Val |
| | | | 275 | | | | | 280 | | | | | 285 | |
| His | Asn | Ala | Lys | Thr | Lys | Pro | Arg | Glu | Glu | Gln | Tyr | Asn | Ser | Thr |
| | | | 290 | | | | | 295 | | | | | 300 | |
| Tyr | Arg | Val | Val | Ser | Val | Leu | Thr | Val | Leu | His | Gln | Asp | Trp | Leu |
| | | | 305 | | | | | 310 | | | | | 315 | |
| Asn | Gly | Lys | Glu | Tyr | Lys | Cys | Lys | Val | Ser | Asn | Lys | Ala | Leu | Pro |
| | | | 320 | | | | | 325 | | | | | 330 | |
| Ala | Pro | Ile | Glu | Lys | Thr | Ile | Ser | Lys | Ala | Lys | Gly | Gln | Pro | Arg |
| | | | 335 | | | | | 340 | | | | | 345 | |
| Glu | Pro | Gln | Val | Tyr | Thr | Leu | Pro | Pro | Ser | Arg | Glu | Glu | Met | Thr |
| | | | 350 | | | | | 355 | | | | | 360 | |
| Lys | Asn | Gln | Val | Ser | Leu | Thr | Cys | Leu | Val | Lys | Gly | Phe | Tyr | Pro |
| | | | 365 | | | | | 370 | | | | | 375 | |
| Ser | Asp | Ile | Ala | Val | Glu | Trp | Glu | Ser | Asn | Gly | Gln | Pro | Glu | Asn |
| | | | 380 | | | | | 385 | | | | | 390 | |
| Asn | Tyr | Lys | Thr | Thr | Pro | Pro | Val | Leu |
| | | | 395 | | | | | 400 |

-continued

```
Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 4
<211> LENGTH: 213
<212> TYPE: PRT
<213> ORGANISM: Homo sapiens
<220> FEATURE:
<221> NAME/KEY: CR4098 light chain
<222> LOCATION: (1)..(213)

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Pro
                85                  90                  95

Thr Phe Gly Gly Gly Thr Lys Val Glu Ile Lys Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

US 7,959,922 B2

LIQUID ANTI-RABIES ANTIBODY FORMULATIONS

CROSS-REFERENCE TO RELATED APPLICATION

This application is the national entry of PCT International Patent Application PCT/EP2007/063244, filed on Dec. 4, 2007 designating the United States of America, published in English as WO2008/068246 A1, which, under 35 USC §119, claims the benefit of both U.S. Provisional Patent Application U.S. Ser. No. 60/872,892 filed Dec. 6, 2006 and EP 06125400.9 filed on Dec. 5, 2006.

FIELD OF THE INVENTION

The invention relates to medicine. In particular the invention is directed to stable formulations of specific anti-rabies antibodies.

BACKGROUND OF THE INVENTION

In the past ten years, advances in biotechnology have made it possible to identify, develop and produce a variety of antibodies for use in the diagnosis, prevention, and treatment of many different diseases and disorders. Examples of such antibodies are the anti-rabies virus antibodies described in WO 2005/118644. An antibody cocktail with two such antibodies, CR57 and CR4098, is particularly advantageous and can be used in rabies post-exposure prophylaxis. In WO 2005/118644, these antibodies were prepared and used in PBS.

Like any protein, the biological activity of an antibody, such as its binding affinity or neutralizing activity, depends upon the conformational integrity of at least a core sequence of amino acids remaining intact while protecting the protein's multiple functional groups from degradation. Chemical and physical instability can each contribute to degradation of an antibody. Because antibodies are larger and more complex than traditional organic and inorganic drugs, the formulation of such antibodies poses special problems. Antibody stability can be affected by such factors as ionic strength, pH, temperature, repeated cycles of freeze/thaw, antibody concentration and shear forces. Active antibodies may be lost as a result of physical instabilities, including denaturation, aggregation (both soluble and insoluble aggregate formation), precipitation and adsorption as well as chemical instabilities, including, for example, racemization, beta-elimination or disulfide exchange, hydrolysis, deamidation, and oxidation, to name just a few. Any of these instabilities can potentially result in the formation of antibody by-products or derivatives having lowered biological activity, increased toxicity, and/or increased immunogenicity.

While the prior art indicates numerous examples of excipients that can be suitably employed to create antibody formulations for specific antibodies, it is impossible to predict which excipients should be added and in what amount they should be added to overcome the particular instability problems that a particular antibody may have. Furthermore, it is difficult to find optimal conditions, such as antibody concentration, pH and storage temperature, that keep a particular antibody chemically and biologically stable within a particular formulation. In view of all the factors that can be varied, finding suitable excipients and optimal conditions for formulating a single monoclonal antibody is fraught with challenges. Obviously, finding suitable excipients and optimal conditions for formulating two different monoclonal antibodies in a single formulation is even more difficult and problematic. Notably, the art does not provide a long-term stable pharmaceutical preparation containing two different recombinant monoclonal antibodies.

Accordingly, there existed a need in the art to find formulations wherein not only a single monoclonal antibody, but even two different specific monoclonal antibodies against rabies virus, are stable on storage over a prolonged period of time. The storage stability should also be retained in the case of shear forces acting during transport and under modified climatic conditions, in particular at elevated temperature and atmospheric humidity. Furthermore, the formulation should be suitable for the intended route of administration, should be well tolerated and should have a simple structure.

It is an object of the invention to provide such formulations.

SUMMARY OF THE INVENTION

Formulations that meet the requirements of the object of the invention have surprisingly been found in the form of aqueous solutions that in addition to the two different monoclonal antibodies, comprise citrate buffer, a tonicity agent and a surfactant. Phosphate buffer was surprisingly found to lead to instability of the specific antibodies, which instability was even increased by addition of surfactant. The invention thus provides formulations for the specific anti-rabies antibodies CR57 and CR4098, or functional variants thereof. The invention also pertains to antibody formulations comprising both CR57 and CR4098, or functional variants thereof. The formulations contain, besides the active ingredient (the antibody or antibodies), a citrate buffer, a tonicity agent and a surfactant. The formulations of the invention are stable for at least 1 year at −70° C. and at 5° C.

DETAILED DESCRIPTION OF THE INVENTION

Figure 1:
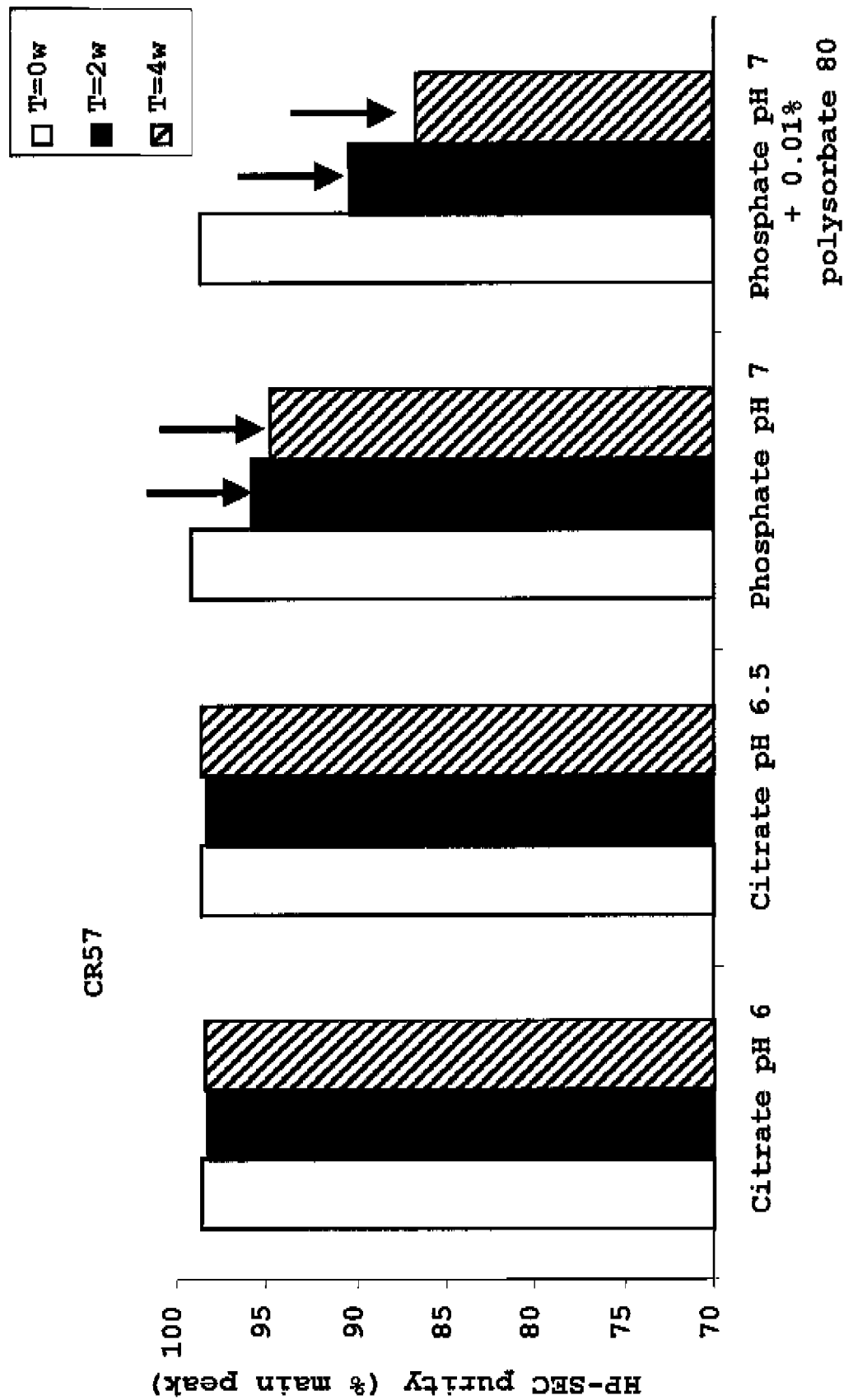
FIG. 1. The stability of anti-rabies virus antibody CR57 after storage for 0 (white columns), 2 (black columns) and 4 weeks (shaded columns) at 40.+−.2.degree.C./75.+−.5% relative humidity as measured by HP-SEC is shown. From left to right the following buffer systems were tested: citrate (20 mM, pH 6.0); citrate (20 mM, pH 6.5); phosphate (20 mM, pH 7.0); phosphate (20 mM, 0.01% w/v polysorbate 80, pH 7.0).

The formulations of the invention comprise at least one of, and preferably both of, antibody CR57 (heavy chain SEQ ID NO: 1 and light chain SEQ ID NO: 2) and antibody CR4098 (heavy chain SEQ ID NO: 3 and light chain SEQ ID NO: 4). Identification, isolation, preparation and characterization of the anti-rabies virus monoclonal antibodies CR57 and CR4098 has been described in detail in U.S. Pat. No. 7,579,446, corresponding to WO 2005/118644, which U.S. patent is incorporated herein by reference. Functional variants of these antibodies may have similar physicochemical properties based on their high similarity and therefore are also included within the scope of the invention. Functional variants are defined for the present invention as antibodies with an amino acid sequence that is at least 95%, preferably at least 97%, for instance at least 98% or 99% homologous to CR57 or CR4098, and capable of competing for binding to the target recognized by the parent molecule (the parent molecule being CR57 or CR4098, respectively) and having rabies virus neutralizing activity. A target for an antibody is an antigen (for the present antibodies this is rabies virus, in particular G protein thereof), and may be further defined as an epitope. The targets of the parent molecules have been disclosed in WO 2005/118644 (U.S. Pat. No. 7,579,446), and determining competition for binding to the target can be done by routine methods known to the skilled person. Preferably the functional variants are human antibodies, and preferably are IgG1 molecules. In preferred embodiments, a functional variant is at least 95%, 97%, 98%, or 99% identical in amino acid sequence with the parent antibody. The term "functional variant", as used herein, thus refers to a monoclonal antibody that comprises an amino acid sequence that is altered by one or more amino acids compared to the amino acid sequences of the parental monoclonal antibody. The functional variant may have conservative sequence modifications including amino acid substitutions, additions and deletions. Amino acid modifications can be introduced by standard techniques known in the art, such as site-directed mutagenesis, molecular cloning, oligonucleotide-directed mutagenesis and random PCR-mediated mutagenesis in the nucleic acid encoding the antibodies. Conservative amino acid substitutions include the ones in which the amino acid residue is replaced with an amino acid residue having similar structural or chemical properties. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine, tryptophan), nonpolar side chains (e.g., glycine, alanine, valine, leucine, isoleucine, proline, phenylalanine, methionine), beta-branched side chains (e.g., threonine, valine, isoleucine) and aromatic side chains (e.g., tyrosine, phenylalanine, tryptophan). It will be clear to the skilled artisan that other classifications of amino acid residue families than the one used above can also be employed. Furthermore, a variant may have non-conservative amino acid substitutions, e.g., replacement of an amino acid with an amino acid residue having different structural or chemical properties. Similar minor variations may also include amino acid deletions or insertions, or both. Guidance in determining which amino acid residues may be substituted, inserted, or deleted without abolishing immunological activity may be found using computer programs well known in the art. Computer algorithms such as inter alia Gap or Bestfit known to a person skilled in the art can be used to optimally align amino acid sequences to be compared and to define similar or identical amino acid residues.

Functional variants may have the same or different, either higher or lower, binding affinities compared to the parental antibody but are still capable of specifically binding to the rabies virus or a fragment thereof, and may have the same, higher or lower, rabies virus neutralizing activity as the parental antibody.

In a specific embodiment the formulation according to the invention comprises a first anti-rabies virus monoclonal antibody that has a kappa light chain and a second anti-rabies virus monoclonal antibody that has a lambda light chain. This allows easy determination of the antibody concentration for each antibody, as specific ELISAs can be performed for each of the kappa and the lambda light chain.

The term "monoclonal antibody" as used herein refers to a preparation of antibody molecules of single molecular composition. A monoclonal antibody displays a single binding specificity and affinity for a particular epitope. The monoclonal antibodies of the invention (CR57 and CR4098 and functional variants thereof) for the formulations of the present invention are human antibodies and are in the IgG class of antibodies, preferably IgG1.

Methods for production of monoclonal antibodies are well known in the art and are described, for example, in Antibodies: A Laboratory Manual, Edited by: E. Harlow and D, Lane (1988), Cold Spring Harbor Laboratory, Cold Spring Harbor, N.Y., which is incorporated herein by reference.

The term "specifically binding" means immunospecifically binding to an antigen or a fragment thereof and not immunospecifically binding to other antigens. A monoclonal antibody that immunospecifically binds to an antigen may bind to other peptides or polypeptides with lower affinity as determined by, e.g., radioimmunoassays (RIA), enzyme-linked immunosorbent assays (ELISA), BIACORE, or other assays known in the art. Monoclonal antibodies or fragments thereof that immunospecifically bind to an antigen may be cross-reactive with related antigens. Preferably, monoclonal antibodies or fragments thereof that immunospecifically bind to an antigen do not cross-react with other antigens.

By "pharmaceutically acceptable excipient" is meant any inert substance that is combined with an active molecule such as monoclonal antibody for preparing an agreeable or convenient dosage form. The "pharmaceutically acceptable excipient" is an excipient that is non-toxic to recipients at the dosages and concentrations employed, and is compatible with other ingredients of the formulation comprising the monoclonal antibody.

The term "by-product" includes undesired products, which detract or diminish the proportion of therapeutic/prophylactic antibody in a given formulation. Typical by-products include aggregates of the antibody, fragments of the antibody, e.g. produced by degradation of the antibody by deamidation or hydrolysis, or mixtures thereof. Typically, aggregates are complexes that have a molecular weight greater than the monomer antibody. Antibody degradation products may include, for example, fragments of the antibody, for example, brought about by deamidation or hydrolysis. Typically, degradation products are complexes that have a molecular weight less than the monomer antibody. In the case of an IgG antibody, such degradation products are less than about 150 kD.

A "stable/stabilized" formulation as used herein is one in which the antibody therein essentially retains its physical stability/identity/integrity and/or chemical stability/identity/integrity and/or biological activity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10:29-90 (1993), for example. Stability can be measured at a selected temperature and other storage conditions for a selected time period. The stability may be determined by at least one of the methods selected from the group consisting of visual inspection, SDS-PAGE, IEF, HPSEC, RFFIT, and kappa/lambda ELISA. A monoclonal antibody "retains its physical stability" in a pharmaceutical formulation, if it shows no signs of aggregation, precipitation and/or denaturation upon visual examination of color and/or clarity, or as measured by UV light scattering, SDS-PAGE or by (high pressure) size exclusion chromatography (HPSEC). Preferably, when using the formulations according to the invention, 5% or less, typically 4% or less, preferably 3% or less, more preferably 2% or less and particularly 1% or less of the antibodies forms aggregates as measured by HPSEC or any other suitable method for measuring aggregation formation. E.g., an antibody is considered stable in a particular formulation if the antibody monomer has a purity of ≧about 90%, preferably ≧about 95%, in particular ≧about 98% as measured by HPSEC after a certain predetermined period of time under certain storage conditions in said particular formulation. Thus, the CR57 and CR4098 antibodies are stable in the formulations of the invention upon storage at 5±3° C. for at least 18 months, i.e. the monomer peak in the HPSEC chromatogram comprises an area of >95% of the total area of all peaks (in Table 9 it can be seen that the main peak area is even >99%). Chemical stability can be assessed by detecting and quantifying chemically altered forms of the protein. Chemical alteration may involve size modification (e.g. clipping) which can be evaluated using (HP)SEC, SDS-PAGE and/or matrix-assisted laser desorption ionization/time-of-flight mass spectrometry (MALDI/TOF MS), for example. Other types of chemical alteration include charge alteration (e.g. occurring as a result of deamidation) which can be evaluated by ion-exchange chromatography, for example. An antibody "retains its biological activity" in a pharmaceutical formulation at a given time, if the biological activity of the antibody at a given time is at least about 90% (within the errors of the assay) of the biological activity exhibited at the time the pharmaceutical formulation was prepared as determined in an antigen binding assay or virus neutralizing assay, for example.

"About" as used in the present application means ±10%, unless stated otherwise.

In a first aspect the invention encompasses a pharmaceutical formulation comprising at least an active ingredient, preferably in a therapeutically effective amount, and at least a pharmaceutically acceptable excipient. Preferably, the pharmaceutical formulation comprises a citrate buffer, a tonicity agent, a surfactant and two anti-rabies virus monoclonal antibodies, wherein the antibodies are different from one another. The formulation may be solid, e.g. frozen or lyophilized, but is preferably liquid, e.g. aqueous. The formulation may comprise at least two distinct anti-rabies virus monoclonal antibodies, in particular (i) CR57 (antibody with amino acid sequence of heavy chain SEQ ID NO: 1 and light chain SEQ ID NO: 2) or a functional variant thereof and (ii) CR4098 (antibody with amino acid sequence of heavy chain SEQ ID NO: 3 and light chain SEQ ID NO: 4) or a functional variant thereof.

In a specific embodiment the formulation according to the invention has a rabies virus neutralizing potency ranging from about 250 IU/ml to about 1500 IU/ml, e.g. from about 300 IU/ml to about 1400 IU/ml, typically from about 380 IU/ml to about 1350 IU/ml. It is well within the reach of a person skilled in the art to measure rabies virus neutralization. Neutralization can for instance be measured as described in Laboratory techniques in rabies, Edited by: F.-X. Meslin, M. M. Kaplan and H. Koprowski (1996), 4th edition, Chapters 15-17, World Health Organization, Geneva. A suitable and known assay for neutralizing activity is a RFFIT assay.

In an embodiment the rabies virus neutralizing potency of the formulations of the invention after 12 months of storage at 5±3° C. is at least 80%, preferably at least 90%, more preferably at least 95%, more preferably at least 98%, and in particular 100% of the rabies virus neutralizing potency of the formulations of the invention before storage. In certain embodiments the rabies virus neutralizing potency of the formulations of the invention after 3 months of storage at 25±2° C. is at least 90%, preferably at least 95%, more preferably at least 98%, and in particular 100% of the rabies virus neutralizing potency of the formulations of the invention before storage.

The formulations according to the invention comprise a surfactant, also known as stabilizer. Surfactants may include, but are not limited to, polysorbates. The skilled person is aware that other surfactants, e.g. non-ionic or ionic detergents, can be used as surfactants as long as they are pharmaceutically acceptable, i.e. suitable for administration to humans. In a preferred embodiment the invention provides a formulation according to the invention, wherein the surfactant is a polysorbate such as polysorbate 20, polysorbate 40, polysorbate 60, polysorbate 65 or polysorbate 80, with polysorbate 80 being preferred. In an embodiment the polysorbate 80 is present in the formulations in an amount from about 0.0005% w/v to about 0.05% w/v, preferably from about 0.005% w/v to about 0.03% w/v, more preferably from about 0.008% w/v to about 0.015% w/v. In a preferred embodiment polysorbate 80 is present in an amount of about 0.01% w/v.

In certain embodiments, the invention provides formulations according to the invention, wherein the citrate buffer, e.g. sodium citrate dehydrate (2.5 mg/ml)/citric acid monohydrate (0.3 mg/ml) buffer, is present at a concentration from about 5 mM to about 25 mM, preferably from about 7 mM to about 20 mM, more preferably from about 8 mM to about 15 mM, and particularly from about 9 mM to about 12 mM. In a preferred embodiment the citrate buffer is present at a concentration of about 10 mM.

In certain embodiments the invention is concerned with formulations according to the invention, wherein the pH ranges from about 5.2 to about 6.8, typically from about 5.5 to about 6.5, preferably from about 5.7 to about 6.3, more preferably from about 5.8 to about 6.2 and particularly from about 5.9 to about 6.1. In a preferred embodiment the pH is about 6.0.

In a specific, non-limiting, embodiment the tonicity agent is sodium chloride. Other salts can for instance also be used as tonicity agents, or for instance sugars, and the like, as long as they are pharmaceutically acceptable, as is known to the skilled person. In certain embodiments of the invention, the tonicity agent is present at a concentration from about 50 mM to about 250 mM, typically from about 75 mM to about 225 mM, preferably from about 100 mM to about 200 mM, and more preferably from about 125 mM to about 175 mM. In a preferred embodiment the tonicity agent is present at a concentration of about 150 mM. In certain embodiments the osmolality of the formulations according to the invention ranges from about 250 mOsm/kg to about 350 mOsm/kg, preferably from about 270 mOsm/kg to about 330 mOsm/kg, more preferably from about 280 mOsm/kg to about 320 mOsm/kg, and particularly from about 290 mOsm/kg to about 310 mOsm/kg. In a preferred embodiment the osmolality is about 300 mOsm/kg. In other words, the formulations are preferably substantially isotonic, i.e. having substantially the same osmotic pressure as human blood. Isotonicity can be measured using vapor pressure or ice-freezing type osmometers, for example. The osmolality of the formulations of the invention can for instance be regulated by one or more tonicity agents.

The concentration of each antibody in the formulations of the invention preferably is between about 0.1 and 2.0 mg/ml, typically between about 0.1 and 1 mg/ml. In certain non-limiting embodiments, the concentration of each antibody is 0.15 (±20%) mg/ml. In other non-limiting embodiments each antibody is present in a concentration of 0.3 (±20%) mg/ml (i.e. total 0.6 mg/ml for two antibodies).

In certain embodiments, the (protein) ratio of the two antibodies is between 5:1 and 1:5, preferably between 2:1 and 1:2 and particularly about 1:1.

Furthermore, the formulation according to the invention may comprise other excipients including, but not limited to, amino acids and salts thereof, sugars, proteins, diluents, solubilizing agents, pH-modifiers, soothing agents, additional buffers, other inorganic or organic salts, antioxidants, or the like. Preferably, however, the formulations of the present invention comprise no other excipients next to a citrate buffer, a tonicity agent and a surfactant.

In the formulations according to the invention the anti-rabies virus monoclonal antibodies CR57 and CR4098 are stable at about 2° C. to about 8° C. for at least about 1 year, typically at least about 18 months. Preferably they may be stable at about 2-8° C. for at least about 2 years, more preferably 3 years.

Furthermore, the anti-rabies virus monoclonal antibodies are stable in the formulations according to the invention at about 25±2° C. for at least about 2 months. Besides that, the anti-rabies virus monoclonal antibodies are stable in the formulations according to the invention at about 40±2° C. for at least 2 weeks.

In certain embodiments the formulations are suitable for administering intramuscularly, intradermally, subcutaneously, injected locally into a wound, or a combination thereof. Therefore, the formulations are preferably sterile. Methods for making formulations sterile are well known in the art and include filtration through sterile filtration membranes or autoclaving the ingredients of the formulation, with the exception of the antibodies, at about 120° C. for about 30 minutes, for example.

In preferred embodiments the formulations are substantially free of endotoxin. Endotoxins are low molecular weight complexes of about 10 kDa that are associated with the outer cell wall of gram-negative bacteria that can produce pyrogenic reactions upon parenteral administration to a patient. Accordingly, the FDA has set an upper limit of 5 EU per dose per kilogram body weight in a single one-hour period for intravenous drug applications (see, e.g., The United States Pharmacopeial Convention (USP), Pharmacopeial Forum 26 (1):223 (2000)). In certain embodiments, the formulation has a concentration of endotoxin of less than about 5.0 endotoxin units per milliliter (EU/ml) (a concentration of less than about 5.0 EU/ml is referred to herein as substantially free of endotoxin), preferably less than about 2.5 EU/ml, more preferably less than about 1.0 EU/ml, even more preferably less than about 0.5 EU/ml and particularly less than about 0.30 EU/ml. In certain embodiment, the formulation has a concentration of endotoxin that ranges from about 0.001 EU/ml to about 5.0 EU/ml. Methods for measuring endotoxins are known to a person skilled in the art and include, but are not limited to, gel-clot assays, turbidimetric (spectrophotometric) assays and chromogenic assays.

"Post exposure prophylaxis" (PEP) is indicated for persons possibly exposed to a rabid animal. Possible exposures include bite exposure (i.e. any penetration of the skin by teeth) including animal bites, and non-bite exposure. The formulations according to the invention can be administered to a subject in need thereof for use in prevention and/or treatment, e.g. post exposure prophylaxis, of a rabies virus infection. The formulations of the invention may be employed in conjunction with other molecules useful in diagnosis, prophylaxis and/or treatment of rabies virus. For instance, they can be co-administered with a vaccine against rabies virus. Alternatively, the vaccine may also be administered before or after administration of the formulations of the invention. Administration of the formulations of the invention with a vaccine is suitable for post exposure prophylaxis. Rabies vaccines include, but are not limited to, purified chick embryo cell (PCEC) vaccine (RabAvert, Rabipur), human diploid cell vaccine (HDCV; Imovax vaccine) or rabies vaccine adsorbed (RVA). Preferably, a single bolus of the formulations of the invention are administered. The dosing regimen of post exposure prophylaxis is administration of five doses of rabies vaccine intramuscularly in the deltoid muscle on days 0, 3, 7, 14 and 28 after exposure in individuals not previously immunized against rabies virus. The formulations according to the invention should be administered into and around the wounds on day 0 or otherwise as soon as possible after exposure, with the remaining volume given intramuscularly at a site distant from the vaccine. Non-vaccinated individuals are advised to be administered anti-rabies virus antibodies. A therapeutically effective amount of antibody or antibodies is administered, which amount is effective or at least partially effective for PEP of rabies, i.e. rabies virus is neutralized.

In a further aspect the invention provides a pharmaceutical unit dosage form comprising an effective amount of a formulation according to the invention for post exposure prophylaxis treatment of a subject through administration of the dosage form to the subject. In a preferred embodiment the subject is a human. The human may be an adult or may be an infant. The term "pharmaceutical unit dosage form" as used herein refers to a physically discrete unit suitable as unitary dosages for the subjects to be treated, each unit containing a predetermined quantity of active compound calculated to produce the desired therapeutic/prophylactic effect in association with the required pharmaceutical carrier, diluent, or excipient.

The unit dosage form may be a container comprising the formulation. Suitable containers include, but are not limited to, sealed ampoules, vials, bottles, syringes, and test tubes. The containers may be formed from a variety of materials such as glass or plastic and may have a sterile access port (for example the container may be a vial having a stopper pierceable by a hypodermic injection needle). In a preferred embodiment the container is a vial. The vial preferably comprise a volume from about 0.3 ml to about 3 ml. Preferably, the vial contains anti-rabies virus antibodies in an amount from about 0.1 mg to about 2.0 mg. In an embodiment the vial contains a total of 750-2000 IU of rabies virus neutralizing monoclonal antibodies per vial. This type of vial can suitably be used for administration to an adult, while a vial containing a total of 250-750 IU of rabies virus neutralizing monoclonal antibodies per vial can suitable be used for administration to an infant. The antibodies are typically formulated in the formulations of the invention in a therapeutically effective amount. Dosage regimens can be adjusted to provide the optimum desired response (e.g. a therapeutic response). A suitable dosage range may for instance be 10-30 IU/kg body weight, such as about 20 IU/kg body weight.

The pharmaceutical unit dosage form may be present in a kit, further comprising a instructions for use. The kit may further comprise more containers comprising pharmaceutically acceptable excipients and include other materials desirable from a commercial and user standpoint, including filters, needles, syringes. Associated with the kits can be instructions customarily included in commercial packages of therapeutic, prophylactic or diagnostic products, that contain information about for example the indications, usage, dosage, manufacture, administration, contra-indications and/or warnings concerning the use of such therapeutic, prophylactic or diagnostic products. In certain embodiments the kit comprises instructions to use the appropriate volume necessary to achieve a dose of about 5 IU/kg to about 40 IU/kg, e.g. 20 IU/kg.

Furthermore, the present invention is concerned with a method for improving the storage of two anti-rabies virus monoclonal antibodies in one, e.g. a single, formulation by formulating the antibodies (CR57 and CR4098 or functional variants) in a liquid pharmaceutical formulation according to the invention. The formulation may be stored at a temperature from about 2° C. to about 40° C., e.g. between about 2-8° C. However, the formulations may also be stored at temperatures below 2° C., e.g. at about −20° C., −70° C., etc. By storing the antibodies in the specific formulations according to the invention the amount of by-product formation of the antibodies is reduced. For practical reasons, it is preferred to store the individual antibodies CR57 and CR4098 frozen, e.g. at −70±10° C., before they are mixed, while the final product (cocktail of CR57 and CR4098) is preferably stored in liquid form at 5±3° C.

In a further aspect the invention also pertains to liquid pharmaceutical formulations comprising a single anti-rabies virus monoclonal antibody, i.e. either CR57 or CR4098 or a functional variant of one of these. Preferably, these formulations comprise all features and excipients as described hereinabove. Thus, in preferred embodiments they contain citrate buffer (5-25 mM) and have pH 5.5-6.5, e.g. about 6.0; contain a tonicity agent (e.g. sodium chloride, 50-250 mM, e.g. about 150 mM); comprise a surfactant, e.g. polysorbate 80 (0.0005%-0.05%, e.g. about 0.01%), and are preferably substantially isotonic, sterile and substantially free of endotoxin Features and excipients that might differ from those described above for formulations comprising two different anti-rabies virus monoclonal antibodies are indicated below.

In certain embodiments, formulations according to the invention may comprising a single anti-rabies virus monoclonal antibody in an amount from about 0.1 mg/ml to about 6.0 mg/ml, typically from about 1.0 mg/ml to about 4.0 mg/ml, e.g. from about 2.0 mg/ml to about 3.0 mg/ml. In a specific embodiment the formulation has a rabies virus neutralizing potency ranging from about 300 IU/mg to about 1600 IU/mg, e.g. from about 500 IU/mg to about 1250 IU/mg. Formulations comprising a single antibody as described above may be combined/mixed with one another to obtain the formulations of the invention comprising two antibodies, i.e. an antibody cocktail.

EXAMPLES

To illustrate the invention, the following examples are provided. The examples are not intended to limit the scope of the invention in any way. In general, the practice of the present invention employs, unless otherwise indicated, conventional techniques of chemistry, molecular biology, recombinant DNA technology, immunology such as antibody technology and standard techniques of polypeptide preparation as described in Sambrook, Fritsch and Maniatis, Molecular Cloning: Cold Spring Harbor Laboratory Press (1989); Antibody Engineering Protocols (Methods in Molecular Biology), volume 51, Ed.: Paul S., Humana Press (1996); Antibody Engineering: A Practical Approach (Practical Approach Series, 169), Eds.: McCafferty J. et al., Humana Press (1996); Antibodies: A Laboratory Manual, Harlow and Lane, Cold Spring Harbor Laboratory Press (1999); and Current Protocols in Molecular Biology, Eds. Ausubel et al., John Wiley & Sons (1992), for example.

The amino acid sequences of the CR57 and CR4098 antibodies is shown in Table 10. Identification, cloning, preparation and characterization of these neutralizing anti-rabies virus antibodies has been described in detail in WO 2005/118644. The antibodies were manufactured on a large scale in an essentially similar way. A starting culture of PER.C6 cells stably expressing an anti-rabies virus antibody was thawed, the cells were cultured and cultures were expanded and used to inoculate a bioreactor. The bioreactor was first operated in batch mode followed by fed-batch mode. Medium containing the respective antibody was harvested and clarified by centrifugation and filtrated before further downstream processing. The downstream purification process consisted of standard chromatographic and filtration steps followed by a buffer exchange to formulation buffer lacking polysorbate 80 and concentration to obtain the desired antibody concentration. After addition of polysorbate 80 and filtration, the obtained drug substance (either antibody CR57 or antibody CR4098) was stored at −80° C. until further use. For the manufacture into drug product the drug substances were diluted with formulation buffer, antibody concentrations were measured, and both antibody dilutions were mixed and filtered before final filling.

For stability studies different formulations of the drug substances (single antibodies) and the drug product (cocktail of antibodies) were prepared and analyzed. Samples of the different formulations were analyzed at different time points and temperatures using various analytical methods well known in the art.

HPSEC, SDS-PAGE (reduced and non-reduced), protein concentration (A280), IEF, appearance, pH, and osmolality were used to evaluate the stabilizing effects of the different formulation buffers on the CR57 antibody, the CR4098 antibody and mixtures thereof.

HPSEC was used in part to assess the presence of degradation products of the antibodies due to aggregation or proteolysis. SDS-PAGE was used in part to assess the integrity of the intact antibody and the presence of impurities and potential degradation products. Protein concentration was measured to assess the maintenance of the formulation's protein concentration within an acceptable range. IEF was used to assess the presence and integrity of antibody isoforms that may be present in the formulations and monitor them over time to assess changes that may occur due to deamidation or loss of sialic acid. Appearance of the formulations was conducted based on visual inspection for clarity, color and the presence of particulates. pH was measured to assess the maintenance of the formulation's pH within an acceptable range of about 5.5 to about 6.5. Osmolality was measured to assess the maintenance of the formulation's osmolality within an acceptable range of about 250 mOsm/kg to about 350 mOsm/kg.

Figure 2:
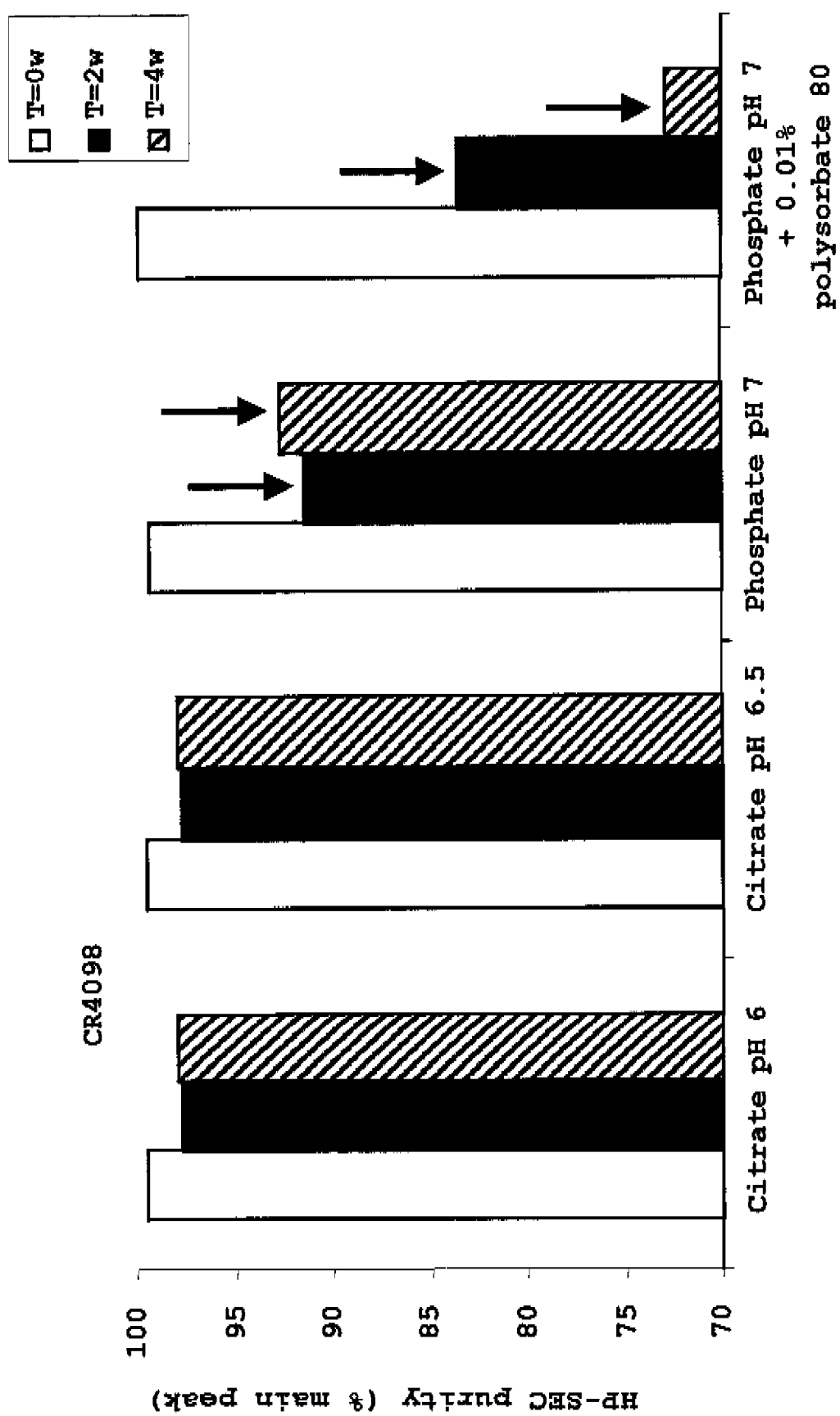
FIG. 2. The stability of anti-rabies virus antibody CR4098 after storage for 0 (white columns), 2 (black columns) and 4 weeks (shaded columns) at 40.+−.2.degree.C./75.+−.5% relative humidity as measured by HP-SEC is shown. From left to right the following buffer systems were tested: citrate (20 mM, pH 6.0); citrate (20 mM, pH 6.5); phosphate (20 mM, pH 7.0); phosphate (20 mM, 0.01% w/v polysorbate 80, pH 7.0).
Figure 3:
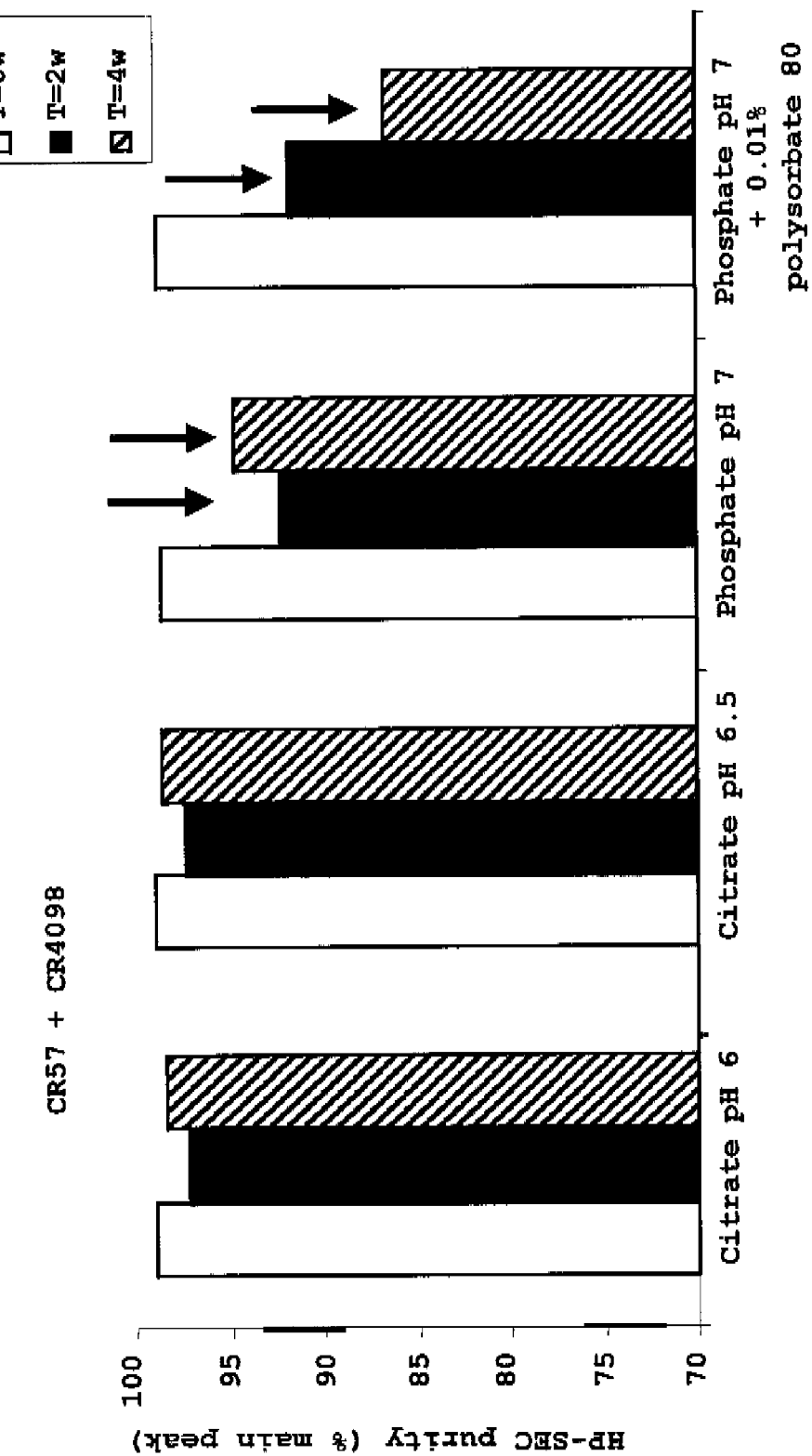
FIG. 3. The stability of a cocktail of CR57 and CR4098 after storage for 0 (white columns), 2 (black columns) and 4 weeks (shaded columns) at 40.+−.2.degree.C./75.+−.5% relative humidity as measured by HP-SEC is shown. From left to right the following buffer systems were tested: citrate (20 mM, pH 6.0); citrate (20 mM, pH 6.5); phosphate (20 mM, pH 7.0); phosphate (20 mM, 0.01% w/v polysorbate 80, pH 7.0).

In a first study different buffer systems were tested. For that purpose anti-rabies virus antibody formulations formulated in citrate buffers were compared to anti-rabies virus antibody formulations formulated in phosphate buffers. Formulations comprising either CR57 (0.1 mg/ml), CR4098 (0.15 mg/ml) or a mixture/cocktail (1:1.5 mixture) of CR57 (0.1 mg/ml) and CR4098 (0.15 mg/ml) in a 20 mM citrate buffer (pH 6.0) or a 20 mM citrate buffer (pH 6.5) were stable upon storage up to 4 weeks at 5±3° C./ambient relative humidity, 25±2° C./60±5% relative humidity and 40±2° C./75±5% relative humidity as indicated by HPSEC analysis. All formulations had a purity of antibody monomer (area %) of >96% as determined by HPSEC (see FIGS. 1-3). Formulations comprising either CR57 (0.1 mg/ml), CR4098 (0.15 mg/ml) or a mixture (1:1.5 mixture) of CR57 (0.1 mg/ml) and CR4098 (0.15 mg/ml) in a 20 mM phosphate buffer (pH 7.0) had a purity of antibody monomer that was significantly lower upon storage for up to 4 weeks at 40±2° C./75±5% relative humidity compared to formulations in the citrate buffers for the same time period and under the same temperature conditions (see FIGS. 1-3). When polysorbate 80 (0.01% w/v) was added to the phosphate buffer, the purity of antibody monomer decreased further to values of about 70% for CR4098 and about 85% for CR57 and the mixture upon storage for up to 4 weeks at 40±2° C./75±5% relative humidity (see FIGS. 1-3). The results clearly show that stability of the separate antibodies as well as the mixture of antibodies is superior in citrate buffers compared to phosphate buffers. In phosphate buffers the antibodies are degraded through fragmentation. The antibodies were equally stable in formulations comprising citrate buffers of pH 6.0 and pH 6.5. Furthermore, it was concluded that addition of polysorbate 80 in phosphate buffers causes additional antibody impurities. The results found with HPSEC were confirmed by other analysis methods including IEF and SDS-PAGE (reduced and non-reduced) (data not shown). Based on the study citrate was used as a buffer system.

To determine optimal surfactant concentration of the formulations, citrate-based formulations comprising different polysorbate 80 concentrations were analyzed (see Table 1). The formulations were prepared as follows. The antibodies CR57 and CR4098 (drug substances) were prepared essentially as described above. They were filtered with a 0.1 µm filter. Protein concentration was the same before and after filtration as measured by A280 protein concentration determination. The concentration of CR57 was 2.5 mg/ml and the concentration of CR4098 was 1.0 mg/ml. Next, a buffer containing 10 mM citrate (pH 6.0) and 50 mM sodium chloride and a buffer containing 10 mM citrate (pH 6.0), 50 mM sodium chloride and 5% polysorbate 80 were prepared. The formulations were prepared as described in Table 2. The final volume was reached with a buffer containing 10 mM citrate (pH 6.0) and 50 mM sodium chloride. The osmolality of all formulations was determined and sodium chloride was added to bring the formulations to an osmolality of about 300 mOsm/kg (iso-osmotic), i.e. the final concentration of sodium chloride in the formulations was 150 mM. Finally, all formulations were filtered with 0.22 µm filters and filled out (400 µl) into 2 ml Eppendorf cups for all tests with the exception of the appearance test, shake study and pH analysis, wherein use was made of 5 ml injection vials (filled with 2 ml sample) capped with 20 mm stoppers and sealed with aluminum caps. The formulations were stored in stability cabinets at 5±3° C./ambient relative humidity, 25±2° C./60±5% relative humidity, or 40±2° C./75±5% relative humidity. At indicated time points two samples were taken and analyzed in monoplo according to the schedule as shown in Table 3.

As already indicated above, protein concentration was the same before and after filtration as measured by A280 protein concentration determination.

The results of the HPSEC analysis are shown in Table 4. The protein components were separated through HPSEC using an isocratic elution method, which allows rapid analysis and high resolution of protein components and also has an improved reproducibility. The results show that at t=0 weeks all formulations had a purity as determined by HPSEC of 98-100%. All formulations showed a comparable purity at t=13 weeks (and all intermediate time points between t=0 and t=13 weeks) compared to t=0 weeks at 5±3° C./ambient relative humidity (i.e. 2-8° C./ambient relative humidity), indicating stability at this temperature for at least 13 weeks. Only for formulation 2 the purity at t=8 and t=13 weeks was just below 98%. Moreover, it was concluded from Table 4 that at 25±2° C./60±5% relative humidity all formulations at all time points showed a purity higher than 95%, indicating that the antibodies are also stable for at least 13 weeks at this temperature. At an elevated temperature of 40±2° C./75±5% relative humidity all formulations showed a purity of >95% in the first two weeks, indicating that the antibodies are stable for at least two weeks at this elevated temperature. At all time points beyond two weeks all formulations showed a purity higher than about 90%, indicating that the antibodies are relatively stable for at least 13 weeks at this elevated temperature. The impurities found with this method included aggregates and fragments of the antibody monomers. The results further indicated that formulations with 0.01% (w/v) polysorbate 80 had a higher purity than similar formulations with 0.03% (w/v) polysorbate 80 (compare purity of formulation 1 with 2, formulation 3 with 4, and formulation 5 with 6). The same impurities were observed for both polysorbate concentrations.

Results of the SDS-PAGE analysis were consistent with the data found with HPSEC. On the basis of non-reduced and reduced SDS-PAGE analysis, the formulations stored at 5±3° C./ambient relative humidity and 25±2° C./60±5% relative humidity showed no signs of significant degradation at all time points when compared to a reference standard, while some minor degradation was found at the different time points of the formulations stored at 40±2° C./75±5% relative humidity (data not shown). No differences for all formulations were observed between the different polysorbate 80 concentrations.

The identification of the antibody samples through SDS-PAGE only confirms the integrity of the antibodies, but it does not illustrate their native or denatured state. IEF illustrates the pI of the antibodies and is also helpful in indicating the conformational microheterogenicity of the antibodies. The combination of IEF with SDS-PAGE is a powerful tool for the detection of even small differences in antibody structures and properties. Based on the IEF results, for all formulations no significant differences were found between the different polysorbate 80 concentrations (data not shown). When the formulations were stored at 40±2° C./75±5% relative humidity, minor degradation (most likely due to deamidation) was observed from time point t=6 weeks on.

The visual inspection of the clarity and color of all formulations stored at 5±3° C./ambient relative humidity, 25±2° C./60±5% relative humidity and 40±2° C./75±5% relative humidity showed that the formulations were practically free of particles up to t=13 weeks, although it was observed that the amount of formulations with particles increased slightly when stored at higher temperatures. The formulations comprising CR57 and CR4098 and 0.01% (w/v) polysorbate 80 contained less particles compared to the formulations comprising CR57 and CR4098 and 0.03% (w/v) polysorbate 80. The shake study indicated no differences between each of the formulations with respect to appearance. The pH values of all formulations did not significantly change during storage at the indicated temperatures and time periods.

The osmolality values of all formulations showed a very small increase during the stability study when kept at 25±2° C./60±5% relative humidity and 40±2° C./75±5% relative humidity. There was no significant difference between formulations comprising 0.01% (w/v) polysorbate 80 compared to formulations comprising 0.03% (w/v) polysorbate 80.

Overall, the results from the study show that single anti-rabies virus antibodies as well as mixtures/cocktails of anti-rabies virus antibodies have the best stability after 13 weeks at 5±3° C./ambient relative humidity, 25±2° C./60±5% relative humidity and 40±2° C./75±5% relative humidity in citrate-based formulations comprising 0.01% (w/v) polysorbate 80.

In a further study formulations comprising citrate (10 mM, pH 6.0), sodium chloride (150 mM), 0.01% (w/v) polysorbate 80 and the single antibody CR57 (1.2 mg/ml) or CR4098 (1.2 mg/ml) were studied when stored under the following two temperatures, 5±3° C. and −70±10° C. Formulations were filled out (250 μl) into 1.2 ml tubes for IEF, SDS-PAGE (reduced and non-reduced) and HPSEC analyses. For pH and appearance analyses 2 ml tubes filled with 2 ml formulation were used. The formulations were stored in stability cabinets at 5±3° C. or −70±10° C. At indicated time points (1, 2 and 3 months) samples were taken and analyzed. The results of the study can be found in Tables 5 and 6.

SDS-PAGE analysis (both reduced and non-reduced) of CR57 and CR4098 formulations at both temperatures indicated that the integrity of the antibodies remained intact for a period of at least 3 months, as no additional degradation bands were observed compared to t=0 months. These results were confirmed by both IEF and HPSEC analysis showing that the antibody structure and aggregate level, respectively, after 3 months at 5±3° C./ambient relative humidity or −70±10° C. was no different from t=0 months. In addition, protein concentration and pH did not significantly change over time. Visual inspection of each formulation showed a clear colorless liquid, practically free from particles.

Analysis of formulations stored at −70±10° C. that were subjected to an additional freeze/thaw cycle after 1 month or 3 months storage showed no differences compared to t=0 months based on the above-mentioned assays, i.e. SDS-PAGE (reduced and non-reduced), HPSEC, IEF, appearance, OD280, and pH (data not shown).

In summary, the results indicate that the antibodies CR57 and CR4098 are stable at 5±3° C./ambient relative humidity and at −70±10° C. in formulations comprising citrate buffer (10 mM, pH 6.0), polysorbate 80 (0.01% w/v) and sodium chloride (150 mM), thereby confirming the results described above. In addition, an additional freeze/thaw cycle after long-term storage (t=1 or t=3 months) of antibody samples stored at −70±10° C. has no influence on the stability of antibody CR57 or CR4098.

In a similar stability study formulations comprising citrate (10 mM, pH 6.0), sodium chloride (150 mM), 0.01% (w/v) polysorbate 80 and the single antibody CR57 (2.47 mg/ml) or CR4098 (2.48 mg/ml) were studied when stored under two different temperatures, i.e. 5±3° C. and −70±10° C., for an even longer period than 3 months. Formulations were filtered through a 0.22 μm filter and filled out in polypropylene tubes (4 ml). In addition, the combination of CR57 and CR4098 at a 1:1 ratio based on protein content (0.3 mg/ml of each antibody resulting in overall protein concentration of 0.6 mg/ml) was studied when stored under two different temperatures, i.e. 5±3° C. and −70±10° C., for up to 6 months. The formulations comprising the cocktail/mixture of antibodies were filtered through a 0.22 μm filter and filled out in glass vials (2.6 ml). The formulations were tested using the following analysis methods: SDS-PAGE (reduced and non-reduced), IEF, HPSEC, RFFIT, appearance, pH (see Tables 7 and 8). Formulations with the combination CR57/CR4098 were also tested by kappa/lambda ELISA and osmolality (see Table 9). Moreover, at t=0 months the endotoxin levels of the formulations comprising the single antibodies or the cocktail of antibodies were determined. Endotoxin levels were assessed with a Limulus Amoebocyte Lysate (LAL) assay using a gel-clot technique. The formulation comprising CR57 contained <0.30 EU/ml, the formulation comprising CR4098 contained <0.30 EU/ml and the formulation containing the cocktail of both antibodies contained <0.24 EU/ml. The formulations were stored in stability cabinets at −70±10° C., 5±3° C., 25±2° C. or 40±2° C. for the indicated time periods.

Formulations containing single antibody were analyzed over a 6 months period and compared to the initial results obtained at t=0 months. IEF and SDS-PAGE band patterns of CR57 and CR4098 formulations stored at −70±10° C. and 5±3° C. for 1, 2, 3, and 6 months were comparable to the band patterns of the CR57 and CR4098 formulations at t=0 months, respectively (see Tables 7 and 8). No additional bands were detected. The HPSEC patterns of both antibodies stored at −70±10° C. and 5±3° C. for 6 months compared well with storage at t=0 months. The target specification of "main peak area >95%" was met in all cases. The dimer peak remained <1% (surface area) and no degradation peaks were detected in any of the samples tested.

Based on the results obtained with these three methods, it was concluded that no degradation of both CR57 and CR4098 occurred during 6 months storage at −70±10° C. and 5±3° C. in the indicated formulations.

Moreover, the protein content and the pH of CR57 and CR4098 were stable in the formulations over the tested time period of 6 months, both at −70±10° C. and at 5±3° C. Analysis of potency (RFFIT-assay) indicated an increased potency value for both antibodies at the 2, 3, and 6 month time points compared to t=0 months and t=1 month time point under both conditions tested (i.e., −70±10° C. and 5±3° C.). This apparent increase in potency was caused by an unstable SRIG control sample that was used as a positive reference in the assay (see Laboratory techniques in rabies, Edited by: F.-X. Meslin, M. M. Kaplan and H. Koprowski (1996), 4th edition, Chapters 15-17, World Health Organization, Geneva.). The effect was eliminated by expressing the results as 50% neutralizing end-point titers (data not shown). Based on these results, it was concluded that CR57 and CR4098 show stable end-point titers, hence stable potency, up to at least 6 months at both storage conditions in the indicated formulations.

In summary, based on the results, CR57 and CR4098 are considered to be stable for at least 6 months at the real time storage condition of −70±10° C. as well as at least 6 months at the accelerated condition of 5±3° C. in formulations comprising citrate (10 mM, pH 6.0), sodium chloride (150 mM) and 0.01% (w/v) polysorbate 80.

The stability was analyzed after longer periods. Based on the stability results obtained with SDS-PAGE (NR+R), IEF, HP-SEC, RFFIT, and OD280 it was concluded that both CR57 and CR4098 are stable for at least 18 months at the storage condition of −70±10° C. as well as at for least 12 months (similar results were found after 9 months, data not shown) at the accelerated condition of 5±3° C. in formulations comprising citrate (10 mM, pH 6.0), sodium chloride (150 mM) and 0.01% (w/v) polysorbate 80.

Formulations containing the cocktail of antibodies CR57 and CR4098 were analyzed over a 6 months time period and compared to the initial results obtained at t=0 months. After 6 months, the appearance of the cocktail stored at 5±3° C. and 25±2° C. remained within target specifications, i.e. the cocktail/mixture was a clear and colorless liquid, practically free from particles (see Table 9). Furthermore, it was observed that the antibody cocktail remained within target specifications when stored up to 3 months at 40±2° C.

The pH and osmolality were monitored at t=0 and t=6 months for 5±3° C. and at 25±2° C. and at the 1 and 3 month time point for the study at 40° C.±2° C. All data were within target specifications.

Furthermore, the antibody cocktail showed stable potency up to 6 months at 5±3° C. and 25±2° C. (see Table 9). A slightly lower potency value was obtained after 3 months at 40±2° C. All data were within the target specification of about 380 to about 1350 IU/ml.

The amount of total protein present in the antibody cocktail as determined by OD280 was stable over the tested time period of 3 months at 40±2° C., and 6 months at 5±3° C. and 25±2° C.

The IgG kappa and lambda ELISA results (i.e. presented as the ratio of both antibodies in the antibody cocktail) remained within the target specifications for up to 6 months at 5±3° C. and 25±2° C. and for up to 3 months at 40±2° C. Based on these results it was concluded that the CR57 and CR4098 content in the antibody cocktail does not change over a time period of 6 months at 5±3° C. and 25±2° C. and 3 months at 40±2° C. The IEF gel pattern of antibody cocktail stored at 5±3° C. for 6 months was comparable to that at t=0 months (see Table 9). An additional band was observed after 3 and 6 months in the samples stored at 25±2° C. and several additional bands were detected after 1 and 3 months in the samples stored at 40±2° C. (see Table 9). These additional bands obtained at elevated storage temperatures might be first indications for degradation.

After 6 months, the SDS-PAGE (reduced and non-reduced) banding patterns of the antibody cocktail stored at 5±3° C. were comparable to the banding pattern at t=0 months (see Table 9). No additional bands were detected. Antibody cocktail stored at 25±2° C. for up to 3 months showed under reducing SDS-PAGE conditions a banding pattern identical to the banding pattern at t=0 months. Under non-reducing conditions, a weak band with a size of approximately 43 kDa was observed after storage of 3 months at 25±2° C. After 6 months storage at 25±2° C. reducing and non-reducing SDS-PAGE analysis showed weak bands at ~40 kDa. A similar result was obtained by SDS-PAGE analysis (both reduced and non-reduced) for the antibody cocktail stored at 40±2° C. Furthermore, smaller bands with a size of 10-15 kDa were detected under this storage condition. Based on these results, it was concluded that at 25±2° C. and 40±2° C. some degradation of the heavy and/or light chains of CR57 and CR4098 might take place over time.

The HPSEC patterns of the antibody cocktail stored at 5±3° C. and at 25±2° C. for up to 6 months compare well with the pattern at t=0 months. The target specification of "main peak area >95%" was met in all cases (see Table 9). The dimer peak remained <1% (surface area) and no degradation peaks were detected in any of the samples tested. Antibody cocktail stored at 40±2° C. showed minor degradation after 3 months as well as an slightly increased dimer peak (2.6% (surface area)) compared to antibody cocktails stored at the two lower temperatures. However, even at 40±2° C. the target specification of "main peak area >95%" was met at all storage time periods tested (see Table 9).

Based on the results obtained with the three latter methods it was concluded that no significant degradation of the antibodies in the antibody cocktail occurred during storage for 6 months at 5±3° C. or 25±2° C., while some minor aggregation and degradation was observed after storage for up to 3 months at 40±2° C.

In summary, it was concluded that the antibody cocktail is stable for at least 6 months at the storage condition of 5±3° C. and 25±2° C. and for at least 3 months at the storage condition of 40±2° C.

Based on the results after 12 months (similar results were obtained after 9 months, data not shown) obtained with SDS-PAGE (NR+R), IEF, HP-SEC, RFFIT, kappa/lambda ELISA it was concluded that the antibody cocktail is stable for at least 12 months at the storage condition of 5±3° C.

Based on the results after 18 months obtained with the analytical assays (SDS-PAGE, IEF, HP-SEC, ELISA; data not shown), it was concluded that the antibody cocktail is stable for at least 18 months at the storage condition of 5±3° C.

TABLE 1

Composition of the antibody formulations.

| Number | Antibody | citrate buffer (mM) | NaCl (mM) | Polysorbate 80 (% w/v) | pH |
|---|---|---|---|---|---|
| 1 | 0.3 mg/ml CR57 | 10 | 150 | 0.01 | 6.0 |
| 2 | 0.3 mg/ml CR57 | 10 | 150 | 0.03 | 6.0 |
| 3 | 0.3 mg/ml CR4098 | 10 | 150 | 0.01 | 6.0 |
| 4 | 0.3 mg/ml CR4098 | 10 | 150 | 0.03 | 6.0 |
| 5 | 0.3 mg/ml CR57 + 0.3 mg/ml CR4098 | 10 | 150 | 0.01 | 6.0 |
| 6 | 0.3 mg/ml CR57 + 0.3 mg/ml CR4098 | 10 | 150 | 0.03 | 6.0 |

TABLE 2

Preparation of the formulations.

| Number | Antibody CR57 (2.5 mg/ml) (ml) | Antibody CR4098 (1.0 mg/ml) (ml) | 5% w/v polysorbate 80 (ml) | Final volume (ml) |
|---|---|---|---|---|
| 1 | 4.20 | 0.00 | 0.70 | 35.00 |
| 2 | 4.20 | 0.00 | 2.10 | 35.00 |
| 3 | 0.00 | 10.50 | 0.70 | 35.00 |
| 4 | 0.00 | 10.50 | 2.10 | 35.00 |
| 5 | 4.20 | 10.50 | 0.70 | 35.00 |
| 6 | 4.20 | 10.50 | 2.10 | 35.00 |

TABLE 3

Analysis of samples of the various formulations at the indicated time points and with the indicated methods.

| Time points (weeks) | 5 ± 3° C./ambient relative humidity | 25 ± 2° C./60 ± 5% relative humidity | 40 ± 2° C./75 ± 5% relative humidity |
|---|---|---|---|
| 0 | A-G | A-G | A-G |
| 2 | B, E | B, E | B, E |
| 6 | B-E | B-E | B-E |
| 8 | B-E | B-E | B-E |
| 13 | C-E | C-E | C-E |

A: Protein concentration (A280)
B: HPSEC
C: SDS-PAGE (reduced and non-reduced)
D: IEF
E: Appearance
F: pH
G: Osmolality

TABLE 4

Purity of antibody monomer (area %) as determined by HPSEC.

| Number | Temperature | t = 0 weeks | t = 2 weeks | t = 6 weeks | t = 8 weeks | t = 13 weeks |
|---|---|---|---|---|---|---|
| 1 | 5 ± 3° C./ambient relative humidity | 98.9 | ND | 98.7 | 98.5 | 98.6 |
|   | 25 ± 2° C./60 ± 5% relative humidity | 98.9 | ND | 98.4 | 98.2 | 96.7 |
|   | 40 ± 2° C./75 ± 5% relative humidity | 98.9 | 98.0 | 93.7 | 94.3 | 90.4 |
| 2 | 5 ± 3° C./ambient relative humidity | 98.3 | ND | 98.2 | 96.9 | 97.6 |
|   | 25 ± 2° C./60 ± 5% relative humidity | 98.3 | ND | 97.5 | 96.9 | 95.4 |
|   | 40 ± 2° C./75 ± 5% relative humidity | 98.3 | 97.5 | 93.4 | 94.1 | 89.9 |
| 3 | 5 ± 3° C./ambient relative humidity | 100 | ND | 100 | 100 | 99.9 |
|   | 25 ± 2° C./60 ± 5% relative humidity | 100 | ND | 99.4 | 99.5 | 97.9 |
|   | 40 ± 2° C./75 ± 5% relative humidity | 100 | 99.4 | 92.3 | 94.2 | 91.8 |
| 4 | 5 ± 3° C./ambient relative humidity | 98.6 | ND | 99.1 | 97.9 | 98.6 |
|   | 25 ± 2° C./60 ± 5% relative humidity | 98.6 | ND | 98.5 | 97.8 | 96.8 |
|   | 40 ± 2° C./75 ± 5% relative humidity | 98.6 | 98.5 | 91.9 | 94.4 | 91.6 |
| 5 | 5 ± 3° C./ambient relative humidity | 99.4 | ND | 99.2 | 99.3 | 99.2 |
|   | 25 ± 2° C./60 ± 5% relative humidity | 99.4 | ND | 98.4 | 98.7 | 97.4 |
|   | 40 ± 2° C./75 ± 5% relative humidity | 99.4 | 98.4 | 91.6 | 93.6 | 89.5 |
| 6 | 5 ± 3° C./ambient relative humidity | 99.3 | ND | 99.1 | 98.8 | 99.0 |
|   | 25 ± 2° C./60 ± 5% relative humidity | 99.3 | ND | 98.1 | 98.3 | 96.9 |
|   | 40 ± 2° C./75 ± 5% relative humidity | 99.3 | 98.4 | 91.6 | 93.8 | 90.6 |

ND: Not determined

TABLE 5

Analysis of samples of the various formulations at the indicated time points and with the indicated methods.

| Antibody (storage temp.) | SDS-PAGE reduced | | | | SDS-PAGE non-reduced | | | | HPSEC % monomer Months | | | | IEF | | | |
|---|---|---|---|---|---|---|---|---|---|---|---|---|---|---|---|---|
|  | 0 | 1 | 2 | 3 | 0 | 1 | 2 | 3 | 0 | 1 | 2 | 3 | 0 | 1 | 2 | 3 |
| CR57 (5 ± 3° C.) | — | — | — | — | — | — | — | — | 98.9 | 98.5 | 98.2 | 98.3 | — | — | — | — |
| CR57 (−70 ± 10° C.) | — | — | — | — | — | — | — | — | 98.9 | 98.5 | 98.3 | 98.4 | — | — | — | — |
| CR4098 (5 ± 3° C.) | — | — | — | — | — | — | — | — | 99.7 | 99.4 | 99.2 | 99.6 | — | — | — | — |
| CR4098 (−70 ± 10° C.) | — | — | — | — | — | — | — | — | 99.7 | 98.9 | 99.5 | 99.6 | — | — | — | — |

—: No unexpected bands detected

TABLE 6

Analysis of samples of the various formulations at the indicated time points and with the indicated methods.

| Antibody (storage temp.) | A280 mg/ml (% A320/A280) | | | | Appear. Months | | | | pH | | | |
|---|---|---|---|---|---|---|---|---|---|---|---|---|
| | 0 | 1 | 2 | 3 | 0 | 1 | 2 | 3 | 0 | 1 | 2 | 3 |
| CR57 (5 ± 3° C.) | 1.33 0.40% | 1.40 0.74% | 1.40 1.01% | 1.42 0.59% | + | + | + | + | 6.0 | ND | ND | 5.9 |
| CR57 (−70 ± 10° C.) | 1.33 0.40% | 1.34 1.42% | 1.34 0.60% | 1.34 0.62% | + | + | + | + | 6.0 | ND | ND | 6.0 |
| CR4098 (5 ± 3° C.) | 1.21 0.67% | 1.22 1.02% | 1.31 1.21% | 1.29 0.98% | + | + | + | + | 6.1 | ND | ND | 6.1 |
| CR4098 (−70 ± 10° C.) | 1.21 0.67% | 1.21 1.49% | 1.20 1.37% | 1.24 0.97% | + | + | + | + | 6.1 | ND | ND | 6.1 |

+: Approved (clear colourless and practically free of particles
ND: not determined

TABLE 7

Stability testing of CR57.

| Test | Target specification | Storage condition | t = 0 | 1 month | 3 months | 6 months | 12 months | 18 months |
|---|---|---|---|---|---|---|---|---|
| pH | 6 ± 0.5 | −70° C. | 6.1 | ND | ND | 6.1 | 6.0 | 6.1 |
| | | 5° C. | ND | ND | ND | 6.1 | 6.0 | ND |
| Appearance | Clear colourless liquid, practically free from particles | −70° C. | + | + | + | + | + | + |
| | | 5° C. | ND | + | + | + | + | ND |
| Quantity by OD280 | 1-5 mg/ml | −70° C. | 2.47 | 2.57 | 2.47 | 2.57 | 2.55 | 2.48 |
| | | 5° C. | ND | 2.55 | 2.27 | 2.68 | 2.59 | ND |
| Non-reduced SDS-PAGE | Band pattern conforms to WS# and contains no additional impurity bands | −70° C. | + | + | + | + | + | + |
| | | 5° C. | ND | + | + | + | + | ND |
| Reduced SDS-PAGE | Band pattern conforms to WS# and contains no additional impurity bands | −70° C. | + | + | + | + | + | + |
| | | 5° C. | ND | + | + | + | + | ND |
| IEF | Band pattern conforms to WS# (additional bands to be reported) | −70° C. | + | + | + | + | + | + |
| | | 5° C. | ND | + | + | + | + | ND |
| HP-SEC | Main peak by area % >95% | −70° C. | 99.5 | 99.7 | 99.4 | 99.7 | 99.8 | 99.7 |
| | | 5° C. | ND | 99.6 | 99.4 | 99.6 | 99.4 | ND |
| Potency | 500-1250 IU/mg | −70° C. | 937 | 974 | 1581 | 2130 | 927 | 1440 |
| | | 5° C. | ND | 922 | 1523 | 1629 | 1054 | ND |

ND: Not determined
CR57 Working Standard (WS) and CR4098 WS
+: Conform target specification

TABLE 8

Stability testing of CR4098.

| Test | Target specification | Storage condition | 0 months | 1 month | 3 months | 6 months | 12 months | 18 months |
|---|---|---|---|---|---|---|---|---|
| pH | 6 ± 0.5 | −70° C. | 6.1 | ND | ND | 6.1 | 6.0 | 6.1 |
| | | 5° C. | ND | ND | ND | 6.1 | 6.0 | ND |
| Appearance | Clear colourless liquid, | −70° C. | + | + | + | + | + | + |
| | | 5° C. | + | + | + | + | + | ND |

TABLE 8-continued

Stability testing of CR4098.

| Test | Target specification | Storage condition | 0 months | 1 month | 3 months | 6 months | 12 months | 18 months |
|---|---|---|---|---|---|---|---|---|
| Quantity by OD280 | practically free from particles 1-5 mg/ml | −70° C. | 2.48 | 2.58 | 2.49 | 2.57 | 2.56 | 2.41 |
| | | 5° C. | ND | 2.65 | 2.52 | 3.03 | 2.76 | ND |
| Non-reduced SDS-PAGE | Band pattern conforms to WS# and contains no additional impurity bands | −70° C. | + | + | + | + | + | + |
| | | 5° C. | ND | + | + | + | + | ND |
| Reduced SDS-PAGE | Band pattern conforms to WS# and contains no additional impurity bands | −70° C. | + | + | + | + | + | + |
| | | 5° C. | ND | + | + | + | + | ND |
| IEF | Band pattern conforms to WS# (additional bands to be reported) | −70° C. | + | + | + | + | + | + |
| | | 5° C. | ND | + | + | + | + | ND |
| HP-SEC | Main peak by area % >95% | −70° C. | 99.6 | 99.7 | 99.7 | 99.8 | 99.7 | 99.7 |
| | | 5° C. | ND | 99.7 | 99.5 | 99.5 | 99.3 | ND |
| Potency | 500-1250 IU/mg | −70° C. | 924 | 971 | 1698 | 1695 | 991 | 1093 |
| | | 5° C. | ND | 897 | 1434 | 1645 | 1093 | ND |

ND: Not determined
CR57 Working Standard (WS) and CR4098 WS
+: Conform target specification

TABLE 9

Stability testing of antibody cocktail.

| Test | Target specification | Storage condition | t = 0 months | 1 month | 2 months | 3 months | 6 months | 12 months |
|---|---|---|---|---|---|---|---|---|
| Osmolality | 300 ± 50 mOsmol/kg | 5° C. | 307 | ND | ND | ND | 310 | 315 |
| | | 25° C. | ND | ND | ND | ND | 314 | ND |
| | | 40° C. | ND | 308 | ND | 312 | ND | ND |
| pH | 6 ± 0.5 | 5° C. | 5.7 | ND | ND | ND | 5.7 | 5.7 |
| | | 25° C. | ND | ND | ND | ND | 5.7 | ND |
| | | 40° C. | ND | 5.7 | ND | 5.8 | ND | ND |
| Appearance | Clear colourless liquid, practically free from particles | 5° C. | + | + | + | + | + | + |
| | | 25° C. | ND | + | + | +[1] | + | ND |
| | | 40° C. | ND | + | ND | + | ND | ND |
| Quantity by OD280 | 0.48-0.72 mg/ml | 5° C. | 0.60 | 0.60 | 0.60 | 0.61 | 0.60 | 0.61 |
| | | 25° C. | ND | 0.61 | 0.60 | 0.60 | 0.60 | ND |
| | | 40° C. | ND | 0.62 | ND | 0.60 | ND | ND |
| CR57/CR4098 ratio | 0.6-1.4 | 5° C. | 0.9 | 0.8 | 0.9 | 0.9 | 0.9 | 1.0 |
| | | 25° C. | ND | 0.8 | 0.9 | 0.9 | 0.9 | ND |
| | | 40° C. | ND | 0.8 | ND | 0.9 | ND | ND |
| Non-reduced SDS-PAGE | Band pattern comparable to WS# and contains no additional impurity bands | 5° C. | + | + | + | + | + | + |
| | | 25° C. | ND | + | + | +[2] | +[4] | ND |
| | | 40° C. | ND | +[2] | ND | +[3] | ND | ND |
| Reduced SDS-PAGE | Band pattern comparable to WS# and contains no additional impurity bands | 5° C. | + | + | + | + | + | + |
| | | 25° C. | ND | + | + | + | +[4] | ND |
| | | 40° C. | ND | +[2] | ND | +[5] | ND | ND |
| HP-SEC | Main peak area % >95% | 5° C. | 99.6 | 100 | 99.5 | 99.5 | 99.9 | 99.2 |
| | | 25° C. | ND | 99.6 | 99.5 | 99.5 | 99.4 | ND |
| | | 40° C. | ND | 99.0 | ND | 95.1 (degr. peak of 2.6%) | ND | ND |

TABLE 9-continued

Stability testing of antibody cocktail.

| Test | Target specification | Storage condition | t = 0 months | 1 month | 2 months | 3 months | 6 months | 12 months |
|---|---|---|---|---|---|---|---|---|
| IEF | Band pattern conforms to WS# (additional bands to be reported) | 5° C. | + | + | + | + | + | + |
| | | 25° C. | ND | + | + | +[6] | +[7] | ND |
| | | 40° C. | ND | +[8] | ND | +[9] | ND | ND |
| Potency | 380-1350 IU/ml | 5° C. | 1006 | 933 | 1089 | 1401 | 999 | 830 |
| | | 25° C. | ND | 937 | 1015 | 1001 | 847 | ND |
| | | 40° C. | ND | 807 | ND | 621 | ND | ND |
| Sterility | Complies | 5° C. | + | ND | ND | ND | ND | + |

ND: Not determined
Working Standard (WS) CR57 and CR4098 antibody cocktail
+: Conform target specification
+[1]: Clear colourless liquid, >10 particles/ml
+[2]: Band pattern comparable to WS# and contains weak additional impurity band with size of about 43 kDa
+[3]: Band pattern comparable to WS# and contains weak additional impurity bands with size of about 10, 15 and 43 kDa
+[4]: Deviant, weak bands appear around 40 kDa
+[5]: Band pattern comparable to WS# and contains weak additional impurity bands with size of about 10 kDa, 15 kDa and between 25-50 kDa
+[6]: Band pattern conforms to WS#; higher staining intensity of bands in the 8.0-8.5 pI-area
+[7]: Deviant, weak bands appear below pI 7.5, different staining intensity in the 8.0-8.5 pI-area
+[8]: Band pattern conforms to WS# and weak additional bands (pI 7.2, 7.3, 8.6)
+[9]: Band pattern conforms to WS# and weak additional bands (pI range 6.3-7.4 and pI 8.6)

TABLE 10

Sequences of CR57 and CR4098

A. CR57 heavy chain

```
                                                           (SEQ ID NO: 1)
QVQLVQSGAE VKKPGSSVKV SCKASGGTFN RYTVNWVRQA PGQGLEWMGG IIPIFGTANY    60
AQRFQGRLTI TADESTSTAY MELSSLRSDD TAVYFCAREN LDNSGTYYYF SGWFDPWGQG   120
TLVTVSSAST KGPSVFPLAP SSKSTSGGTA ALGCLVKDYF PEPVTVSWNS GALTSGVHTF   180
PAVLQSSGLY SLSSVVTVPS SSLGTQTYIC NVNHKPSNTK VDKRVEPKSC DKTHTCPPCP   240
APELLGGPSV FLFPPKPKDT LMISRTPEVT CVVVDVSHED PEVKFNWYVD GVEVHNAKTK   300
PREEQYNSTY RVVSVLTVLH QDWLNGKEYK CKVSNKALPA PIEKTISKAK GQPREPQVYT   360
LPPSREEMTK NQVSLTCLVK GFYPSDIAVE WESNGQPENN YKTTPPVLDS DGSFFLYSKL   420
TVDKSRWQQG NVFSCSVMHE ALHNHYTQKS LSLSPGK                            457
``` light chain

```
                                                           (SEQ ID NO: 2)
QSALTQPRSV SGSPGQSVTI SGTGTSSDIG GYNFVSWYQQ HPGKAPKLMI YDATKRPSGV    60
PDRFSGSKSG NTASLTISGL QAEDEADYYC CSYAGDYTPG VVFGGGTKLT VLGQPKAAPS   120
VTLFPPSSEE LQANKATLVC LISDFYPGAV TVAWKADSSP VKAGVETTTP SKQSNNKYAA   180
SSYLSLTPEQ WKSHRSYSCQ VTHEGSTVEK TVAPTECS                           218
```

B. CR4098 heavy chain

```
                                                           (SEQ ID NO: 3)
QVQLVESGGG AVQPGRSLRL SCAASGFTFS SYGMHWVRQA PGKGLEWVAV ILYDGSDKFY    60
ADSVKGRFTI SRDNSKNTLY LQMNSLRAED TAVYYCAKVA VAGTHFDYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSREEM   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                     449
``` light chain

```
                                                           (SEQ ID NO: 4)
DIQMTQSPSS LSASVGDRVT ITCRASQGIR NDLGWYQQKP GKAPKLLIYA ASSLQSGVPS    60
RFSGSGSGTD FTLTISSLQP EDFATYYCQQ LNSYPPTFGG GTKVEIKTVA APSVFIFPPS   120
DEQLKSGTAS VVCLLNNFYP REAKVQWKVD NALQSGNSQE SVTEQDSKDS TYSLSSTLTL   180
SKADYEKHKV YACEVTHQGL SSPVTKSFNR GEC                                213
```

The invention claimed is:

1. A pharmaceutical formulation of anti-rabies monoclonal antibodies that is stable for at least 12 months at a temperature between about 2° C. to about 8° C., the formulation comprising:
  (i) anti-rabies virus monoclonal antibody CR57 (heavy chain SEQ ID NO: 1 and light chain SEQ ID NO: 2), or an antibody that is at least 95% homologous in sequence thereto and is capable of competing for binding to a target recognized by CR57 and having rabies virus neutralizing activity; and
  (ii) anti-rabies virus monoclonal antibody CR4098 (heavy chain SEQ ID NO: 3 and light chain SEQ ID NO: 4), or an antibody that is at least 95% homologous in sequence thereto and is capable of competing for binding to a target recognized by CR4098 and having rabies virus neutralizing activity;
  wherein the formulation comprises a citrate buffer at a concentration from about 5 mM to about 25 mM, sodium chloride at a concentration from about 50 mM to about 250 mM, and a surfactant.

2. The formulation according to claim 1, wherein the pH ranges from about 5.5 to about 6.5.

3. A formulation of anti-rabies monoclonal antibodies that is stable for at least 12 months at a temperature between about 2° C. to about 8° C., the formulation comprising:
   (i) anti-rabies virus monoclonal antibody CR57 (heavy chain SEQ ID NO: 1 and light chain SEQ ID NO: 2), or an antibody that is at least 95% homologous in sequence thereto and is able to compete for binding to a target recognized by CR57 and having rabies virus neutralizing activity; and
   (ii) anti-rabies virus monoclonal antibody CR4098 (heavy chain SEQ ID NO: 3 and light chain SEQ ID NO: 4), or an antibody that is at least 95% homologous in sequence thereto and is able to compete for binding to a target recognized by CR4098 and having rabies virus neutralizing activity;
   wherein the formulation comprises a citrate buffer, a tonicity agent, and a surfactant, wherein the surfactant is a polysorbate.

4. The formulation according to claim 3, wherein polysorbate 80 is present in an amount from about 0.005% w/v to about 0.05% w/v.

5. The formulation of claim 3, wherein the osmolality of the formulation ranges from about 250 mOsm/kg to about 350 mOsm/kg.

6. The formulation of claim 1, wherein the two anti-rabies virus monoclonal antibodies each are present in an amount from about 0.1 mg/ml to about 2.0 mg/ml.

7. The formulation of claim 1, wherein the formulation has a rabies virus neutralizing potency ranging from about 250 IU/ml to about 1500 IU/ml.

8. The formulation of claim 1, wherein the ratio of the two antibodies is between 5:1 and 1:5.

9. The formulation of claim 1, wherein the formulation is sterile.

10. The formulation of claim 1, wherein the formulation is substantially free of endotoxin.

11. The formulation of claim 1, wherein the formulation has a purity of antibody monomer of at least 95% as determined by HPSEC after two weeks storage at a temperature of 40±2° C. and a relative humidity of 75±5%.

12. A method of post-exposure treatment of a subject, the method comprising:
   administering to the subject a pharmaceutical unit dosage form comprising an effective amount of the formulation of claim 1, for post-exposure prophylaxis treatment of the subject.

13. A method for improving the storage of two anti-rabies virus monoclonal antibodies in one formulation, the method comprising:
   formulating the two anti-rabies virus monoclonal antibodies as the pharmaceutical formulation of claim 1.

14. The method according to claim 13, wherein the formulation is stored at a temperature from about 2° C. to about 40° C.

15. The method according to claim 13, wherein the amount of by-product formation of the antibodies is reduced.

16. The method according to claim 15, wherein 5% or less of the antibodies forms aggregates as measured by HPSEC within 12 months of storage at a temperature from about 2° C. to about 8° C.

17. A pharmaceutical formulation of anti-rabies virus monoclonal antibody CR57 (heavy chain SEQ ID NO: 1 and light chain SEQ ID NO: 2), or an antibody that is at least 95% homologous in sequence thereto and is capable of competing for binding to the target recognized by CR59 and having rabies virus neutralizing activity, which formulation is stable for at least 18 months at a temperature between about 2° C. to about 8° C. and at a temperature between about −60° C. and −80° C., wherein the formulation comprises a citrate buffer at a concentration of from about 5 mM to about 25 mM, sodium chloride at a concentration of from about 50 mM to about 250 mM, and polysorbate 80 in an amount of from about 0.005% w/v to about 0.05% w/v.

18. A pharmaceutical formulation of anti-rabies virus monoclonal antibody CR4098 (heavy chain SEQ ID NO: 3 and light chain SEQ ID NO: 4), or an antibody that is at least 95% homologous in sequence thereto and is capable of competing for binding to the target recognized by CR4098 and having rabies virus neutralizing activity, which formulation is stable for at least 18 months at a temperature between about 2° C. to about 8° C. and at a temperature between about −60° C. and −80° C., wherein the formulation comprises a citrate buffer at a concentration of from about 5 mM to about 25 mM, sodium chloride at a concentration of from about 50 mM to about 250 mM, and polysorbate 80 in an amount of from about 0.005% w/v to about 0.05% w/v.

* * * * *